US010475192B2

(12) United States Patent
Levy

(10) Patent No.: US 10,475,192 B2
(45) Date of Patent: *Nov. 12, 2019

(54) MOTION TRACKING DURING NON-INVASIVE THERAPY

(71) Applicant: Yoav Levy, Hinanit (IL)

(72) Inventor: Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 476 days.

This patent is subject to a terminal disclaimer.

(21) Appl. No.: 15/179,181

(22) Filed: Jun. 10, 2016

(65) Prior Publication Data

US 2017/0358095 A1  Dec. 14, 2017

(51) Int. Cl.
*G06T 7/20* (2017.01)
*A61B 5/00* (2006.01)
(Continued)

(52) U.S. Cl.
CPC ............... *G06T 7/20* (2013.01); *A61B 5/113* (2013.01); *A61B 5/4836* (2013.01); *A61B 5/7292* (2013.01); *A61N 5/1037* (2013.01); *G01R 33/307* (2013.01); *G01R 33/4808* (2013.01); *G01R 33/4814* (2013.01); *G01R 33/56308* (2013.01); *G06T 7/0016* (2013.01); *G06T 11/003* (2013.01); *A61B 5/055* (2013.01);
(Continued)

(58) Field of Classification Search
CPC ............... G06T 7/20; G06T 2211/428; G06T 2207/10088; G06T 2207/20056; G06T 2207/30096; G06T 7/0016; G06T 11/003; A61B 5/113; A61B 5/7292; A61B 5/4836; A61B 2034/2065; A61B 2090/364; A61B 5/055; G01R 33/56509; G01R 33/4824; G01R 33/56308; G01R 33/4808; G01R 33/307; G01R 33/4814; A61N 7/02; A61N 5/1037; A61N 2005/1055
USPC .................................................. 600/407–469
See application file for complete search history.

(56) References Cited

U.S. PATENT DOCUMENTS

2004/0267111 A1\* 12/2004 Feinberg .................. A61B 8/08
600/411
2005/0054910 A1\* 3/2005 Tremblay ............... A61B 5/055
600/411

(Continued)

FOREIGN PATENT DOCUMENTS

DE 102013206315 10/2014

OTHER PUBLICATIONS

International Search Report, for International Application No. PCT/IB2017/000794, dated Oct. 20, 2017, 16 pages.

(Continued)

*Primary Examiner* — Sanjay Cattungal
(74) *Attorney, Agent, or Firm* — Morgan, Lewis & Bockius LLP

(57) ABSTRACT

During a focused-ultrasound or other non-invasive treatment procedure, the motion of the treatment target or other object(s) of interest can be tracked in real time based on (i) the comparison of treatment images against a reference library of images that have been acquired prior to treatment for the anticipated range of motion and have been processed to identify the location of the target or other object(s) therein and (ii) complementary information associated with the stage of the target motion during treatment.

46 Claims, 17 Drawing Sheets

(51) Int. Cl.
| | |
|---|---|
| *G01R 33/30* | (2006.01) |
| *G01R 33/48* | (2006.01) |
| *G06T 7/00* | (2017.01) |
| *G06T 11/00* | (2006.01) |
| *A61B 5/113* | (2006.01) |
| *G01R 33/563* | (2006.01) |
| *A61N 5/10* | (2006.01) |
| *A61B 5/055* | (2006.01) |
| *A61N 7/02* | (2006.01) |
| *G01R 33/565* | (2006.01) |
| *A61B 90/00* | (2016.01) |
| *A61B 34/20* | (2016.01) |

(52) U.S. Cl.
CPC . *A61B 2034/2065* (2016.02); *A61B 2090/364* (2016.02); *A61N 7/02* (2013.01); *A61N 2005/1055* (2013.01); *G01R 33/4824* (2013.01); *G01R 33/56509* (2013.01); *G06T 2207/10088* (2013.01); *G06T 2207/20056* (2013.01); *G06T 2207/30096* (2013.01); *G06T 2211/428* (2013.01)

(56) References Cited

U.S. PATENT DOCUMENTS

| | | | |
|---|---|---|---|
| 2007/0015991 A1* | 1/2007 | Fu | A61B 8/08 600/407 |
| 2009/0088623 A1* | 4/2009 | Vortman | A61B 5/416 600/411 |
| 2011/0178386 A1* | 7/2011 | Grissom | G01R 33/4804 600/410 |
| 2011/0306870 A1* | 12/2011 | Kuhn | A61B 5/0515 600/411 |
| 2013/0090557 A1* | 4/2013 | Takagi | A61B 8/085 600/431 |
| 2013/0150704 A1* | 6/2013 | Vitek | A61B 5/055 600/411 |
| 2013/0251225 A1* | 9/2013 | Liu | G01R 33/5673 382/131 |
| 2014/0018676 A1 | 1/2014 | Kong et al. | |
| 2015/0016682 A1* | 1/2015 | Levy | A61N 7/02 382/103 |
| 2015/0262336 A1* | 9/2015 | Jin | G06T 3/4053 382/275 |
| 2016/0077180 A1* | 3/2016 | Beck | G01R 33/56509 324/309 |
| 2016/0310761 A1* | 10/2016 | Li | A61N 5/1038 |

OTHER PUBLICATIONS

Mougenot, et al., "MRI Guided Focused Ultrasound of Moving Organs: Target Tracking with On-Line Anticipation of Periodic Displacements," Proceedings of the International Society for Magnetic Resonance in Medicine, Joint Annual Meetings ISMRM-ESMRMB, 2007, 1 page.

Fu, et al., "Fiducial-less 2D-3D Spine Image Registration Using Spine Region Segmented in CT Image," Proc. of SPIE, 2007, vol. 6509, pp. 650935-1-10.

Ehrhardt, et al., "Analysis of Free Breathing 1notion Using Artifact Reduced 4D CT Image Data," Proc. of SPIE, 2007, vol. 6512, pp. 65121 N-1-11.

Zur, "Continuous Liver Tracking During Free Breathing MRI Guided Focused Ultrasound," Proceedings of the International Society fr Magnetic Resonance in Medicine, Joint Annual Meetings ISMRM-ESMRMB, 2010, 1 page.

\* cited by examiner

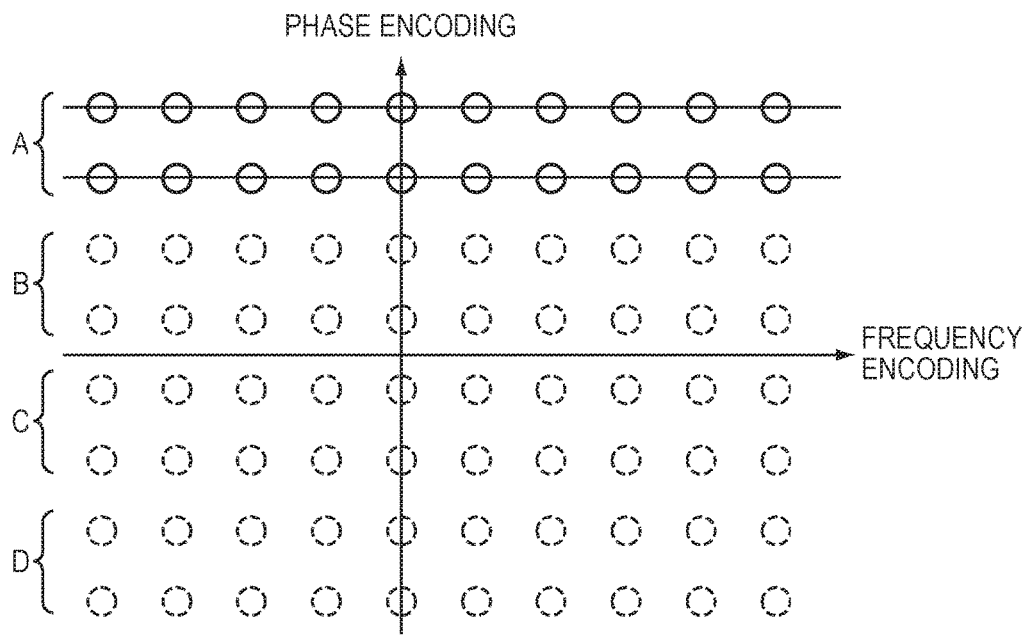
FIG. 5A
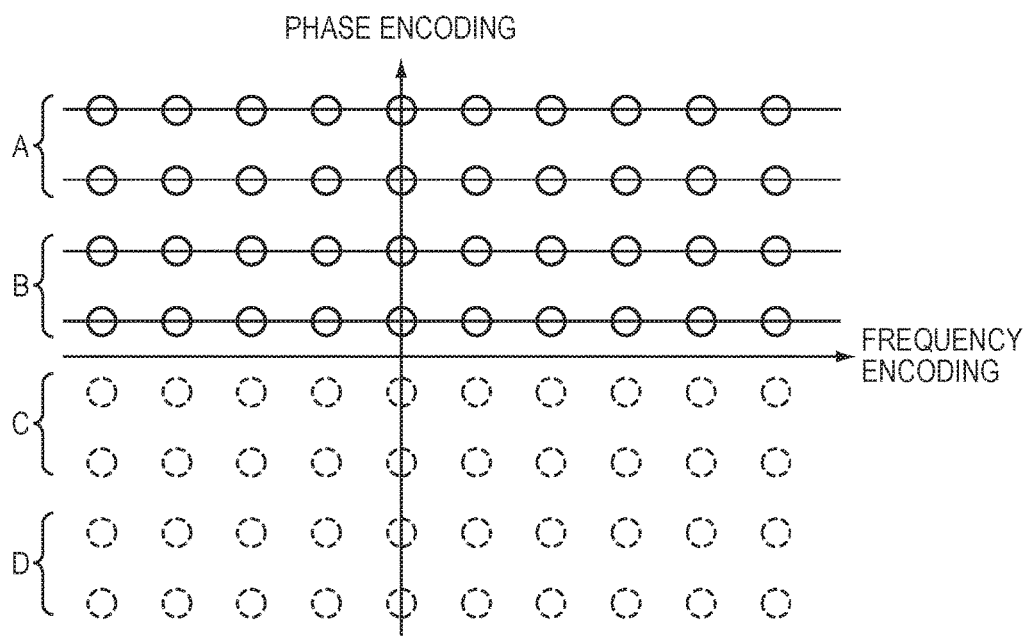
FIG. 5B
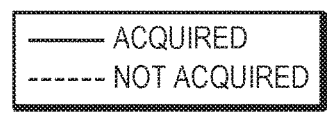

MOTION TRACKING DURING NON-INVASIVE THERAPY

TECHNICAL FIELD

The present invention relates, in general, to tracking moving tissue or organs, and, in particular, to tracking motion thereof during non-invasive therapy.

BACKGROUND

Tissue, such as a benign or malignant tumor or blood clot within a patient's skull or other body region, may be treated invasively by surgically removing the tissue or non-invasively by using, for example, thermal ablation. Both approaches may effectively treat certain localized conditions within the body, but involve delicate procedures to avoid destroying or damaging otherwise healthy tissue. Unless the healthy tissue can be spared or its destruction is unlikely to adversely affect physiological function, surgery may not be appropriate for conditions in which diseased tissue is integrated within healthy tissue.

Thermal ablation, as may be accomplished using focused ultrasound, has particular appeal for treating diseased tissue surrounded by or neighboring healthy tissue or organs because the effects of ultrasound energy can be confined to a well-defined target region. Ultrasonic energy may be focused to a zone having a cross-section of only a few millimeters due to relatively short wavelengths (e.g., as small as 1.5 millimeters (mm) in cross-section at one Megahertz (1 MHz)). Moreover, because acoustic energy generally penetrates well through soft tissues, intervening anatomy often does not impose an obstacle to defining a desired focal zone. Thus, ultrasonic energy may be focused at a small target in order to ablate diseased tissue without significantly damaging surrounding healthy tissue.

An ultrasound focusing system generally utilizes an acoustic transducer surface, or an array of transducer surfaces, to generate an ultrasound beam. The transducer may be geometrically shaped and positioned to focus the ultrasonic energy at a "focal zone" corresponding to the target tissue mass within the patient. During wave propagation through the tissue, a portion of the ultrasound energy is absorbed, leading to increased temperature and, eventually, to cellular necrosis—preferably at the target tissue mass in the focal zone. The individual surfaces, or "elements," of the transducer array are typically individually controllable, i.e., their phases and/or amplitudes can be set independently of one another (e.g., using a "beamformer" with suitable delay or phase shift in the case of continuous waves and amplifier circuitry for the elements), allowing the beam to be steered in a desired direction and focused at a desired distance and the focal zone properties to be shaped as needed. Thus, the focal zone can be rapidly displaced and/or reshaped by independently adjusting the amplitudes and phases of the electrical signal input into the transducer elements.

However, because the human body is flexible and moves even when a patient is positioned to keep still (due to respiration, for example, or small involuntary movements), treatment delivered as multiple sonications over time—even when delivered within seconds of each other—may require interim adjustments to targeting and/or to one or more treatment parameters. Compensation for motion is thus necessary to ensure that the ultrasound beam remains focused on the target and does not damage the surrounding healthy tissues.

Accordingly, an imaging modality, such as magnetic resonance imaging (MRI), may be used in conjunction with ultrasound focusing during non-invasive therapy to monitor the locations of both the target tissue and the ultrasound focus. Generally, an MRI system 100, as depicted in FIG. 1, includes a static-field magnet 102, one or more gradient-field coils 104, a radio-frequency (RF) transmitter 106, and an RF receiver (not shown). (In some embodiments, the same device is used alternately as RF transmitter or receiver.) The magnet includes a region 108 for receiving a patient 110 therein, and provides a static, relatively homogeneous magnetic field over the patient. Time-variable magnetic field gradients generated by the gradient-field coils 104 are superposed with the static magnetic field. The RF transmitter 106 transmits RF pulse sequences over the patient 110 to cause the patient's tissues to emit a (time-varying) RF response signal, which is integrated over the entire (two- or three-dimensional) imaging region and sampled by the RF receiver to produce a time series of response signals that constitute the raw image data. This raw data is passed on to a computation unit 112. Each data point in the time series can be interpreted as the value of the Fourier transform of the position-dependent local magnetization at a particular point in k-space (i.e., wavevector space), where the wavevector k is a function of the time development of the gradient fields. Thus, by Fourier-transforming the time series of the response signal, the computation unit 112 can reconstruct a real-space image of the tissue (i.e., an image showing the measured magnetization-affecting tissue properties as a function of spatial coordinates) from the raw data. The real-space magnetic-resonance (MR) image may then be displayed to the user. The MRI system 100 may be used to plan a medical procedure, as well as to monitor treatment progress during the procedure. For example, MRI may be used to image an anatomical region, locate the target tissue (e.g., a tumor) within the region, guide the beam generated by the ultrasound transducer 114 to the target tissue, and/or monitor the temperature in and surrounding the target tissue.

In image-guided systems, such as MRI-guided focused-ultrasound (MRgFUS) systems), motion compensation is generally accomplished by tracking the target (directly or indirectly) in the images and steering the ultrasound beam based on the tracked position. One approach to target tracking involves determining the coordinates of a set of one or more identifiable features, or "anatomical landmarks," that can be located in each image; and computing the motion of the target, which is presumed to be at a known location relative to the landmarks, based on these coordinates. In an alternative approach, the relative shifts between successive images are determined by correlating one image with a large number of computationally shifted copies of the other image, and selecting the shifted image that provides the best match. In either case, significant image-processing time is expended to determine the target location, reducing the effective imaging rate and often impeding real-time motion compensation. In some cases, delays in recognizing and quantifying target motion cause beam-targeting inaccuracies within a tolerable range. Often, however, it becomes necessary to stop the treatment process and correct for any misalignment due to displacement of the target tissue or organ before treatment can be resumed. This results in significant inefficiencies in the treatment process, and may cause inconvenient delays.

Accordingly, there is a need for improved motion-tracking approaches that facilitate tracking the target, and compensating for its motion, in real time during treatment.

SUMMARY

The present invention provides systems and methods for tracking the motion of a target or other objects of interest in a region of interest in real time during an image-guided treatment procedure or during calibration of an image guided treatment system. In particular, the present invention provides systems and methods for tracking the motion of a treatment target or other objects of interest in an anatomical region of interest in real time during an image-guided treatment procedure. In various embodiments, a library of reference images is acquired using, for example, an MRI apparatus prior to treatment; the reference images cover an anticipated range of a periodic motion (e.g., a complete respiratory cycle) or a non-periodic motion (e.g., a patient's movement). The reference images are then processed to (directly or indirectly) locate the object(s) of interest therein; locational information is stored along with its respective reference image. The reference images may be stored as raw k-space image data and/or reconstructed real-space image data.

During treatment or calibration, in order to track motion of the region of interest (for example an anatomical region of interest or a region of interest within a blank) in real time, an image matrix or a sub-image matrix (i.e., partial data) of the raw k-space image data is acquired repeatedly; in either case, a sub-image matrix may be compared and matched against a corresponding portion of the k-space image data (i.e., data located in the substantially same portion of the k-space) in the reference library to determine image similarity therebetween. Alternatively or additionally, the sub-image matrix may be used to reconstruct a real-space sub-image having a reduced frame size and/or spatial resolution, and the sub-image is compared and matched against the real-space image data in the reference library. Using a sub-image matrix (or partial raw data) for identification purposes obviously reduces acquisition and processing time, but can result in ambiguity: in some instances, more than one image may match the partial raw data (or its reconstructed real-space image). Accordingly, if a sufficiently closely matching reference image is identified without ambiguity (i.e., only one reference image is identified), the location of each object of interest in that reference image is deemed to be the location of the respective object in the treatment sub-image as well. If, however, more than one reference image has sufficiently high similarity (e.g., above a pre-determined threshold) to the treatment sub-image (or sub-image matrix), in various embodiments, complementary information—e.g., additional image-related and/or motion-related information—may be utilized to identify the reference image that best matches the treatment sub-image or sub-image matrix (i.e., to which the treatment sub-image or sub-image matrix most likely corresponds).

Again, once the best-matching reference image is identified, the location of the object(s) of interest in the best-matching reference image is deemed to be the location of the respective object in the treatment sub-image. Thus, compared with conventional tracking approaches, the current invention significantly reduces the image acquisition and processing time required during treatment by acquiring and processing only partial image data (i.e., partial raw k-space data and/or real-space sub-images) that includes the anatomical region of interest, and thus facilitating real-time motion tracking of the object(s) of interest with limited delay. In addition, complementary information including, for example, a stage of the anticipated range of motion, readout from one or more motion sensors, information associated with preceding treatment images, etc., may resolve ambiguity resulting from image comparison using partial data, and thereby correctly identify the reference image best matching the partial raw data and/or sub-image acquired during treatment.

In some embodiments, unlike conventional approaches where the k-space image data is acquired in a continuous row-by-row or column-by-column manner, the image data in k-space in the current invention is alternately acquired in a low frequency region and in a high frequency region. The acquired image data is substantially simultaneously processed to compare against the image data stored in the library upon acquisition and determine whether any reference image(s) are candidate matches. If the number of identified reference image(s) is below a pre-determined threshold (e.g., less than five reference images), complementary information is provided to determine whether one and only one reference image can be identified as the best-matching image. If not, or if the number of identified reference image(s) exceeds the pre-determined threshold, the data acquisition process continues—i.e., alternately acquiring next image data in the low-frequency and high-frequency regions. This step can be iteratively implemented until only one reference image is identified as the image best matching the treatment sub-image. The treatment image data acquired using this approach advantageously includes both high-frequency and low-frequency information, and in some embodiments, the data itself or in combination with the complementary information is sufficient to identify one best-matching reference image without the need for acquiring the entire data to fill in the k-space. Therefore, the present approach can achieve reduced delay in imaging acquisition and significant savings in imaging processing time during treatment.

Accordingly, in one aspect, the invention provides a method for tracking one or more (generally moving) objects of interest (including anatomical objects of interest, for example; a treatment target and/or a non-treatment target) during a treatment sequence. In various embodiments, the method involves, prior to the treatment sequence, acquiring a series of reference images (i.e., at least one image, and typically a plurality of images) of a region (e.g. an anatomical region) that includes the object of interest (e.g. the anatomical object of interest) during motion thereof (each reference image corresponding to a different stage of the motion) and/or acquiring the complementary information during acquisition of the reference images, and processing the images to determine, for each image, a location therein that is associated with the object of interest. Optionally, complementary information, such as a stage of the motion, motion-sensor data, and/or information associated with preceding images (e.g., metadata specifying when during a respiratory cycle the images were obtained) may be acquired during acquisition of the reference images. The method further includes, during the treatment sequence, acquiring treatment images of the anatomical region and acquiring complementary information during acquisition of the treatment images; generally, the treatment images contain less information (e.g., less image data) than the reference images do. One or more of the treatment images are then correlated to the reference image(s) based on similarity therebetween and the complementary information, and subsequently, the object of interest is tracked in the treatment image(s) based at least in part on the location(s) associated with the object in the corresponding reference image(s). As used herein, the term "acquiring" includes obtaining data from sensors or imagers, retrieving data from sources such as reference libraries or treatment images, and computing or deriving new information from existing data. In various embodiments, the method further includes monitoring a temperature in the anatomical region by performing baseline subtraction between the treatment images and the corresponding reference images.

Throughout the disclosure of the present application a "treatment sequence" may be a sequence whereby treatment (for example ultrasound treatment) is carried out or the "treatment sequence" may refer to carrying out a sequence absent any treatment being carried out. Similarly, a "treatment image" refers to an image obtained during a "treatment sequence" with treatment or absent treatment".

Accordingly, the method optionally does not include any treatment. In various embodiments the method is not or does not compromise a method of treatment of the human or animal body. In various embodiments, the images are MRI images, and a sequence for acquiring k-space data associated with the treatment images is determined based on types of information encoded in each k-space location. For example, the k-space data associated with the treatment images is acquired in a high-frequency region and a low-frequency region alternately.

The treatment sequence may include treatment of the anatomical object by, for example, steering a focused ultrasound beam onto the object based on the tracking. Alternatively, the treatment sequence may include treatment of a target other than the anatomical object; during the treatment, a focused ultrasound beam is shaped onto the target so as to avoid the anatomical object based on the tracking. In addition, the treatment sequence may be part of a treatment procedure including multiple time-separated treatment sequences, each having one or more exposures of an anatomical target to therapeutic energy; one or more of the acquired reference images used during a treatment sequence may be the treatment image(s) obtained during a previous treatment sequence. In one embodiment, each exposure is subjection of the anatomical target to acoustic energy.

In some embodiments, the reference images are processed to identify one or more anatomical landmarks in each of the reference images; the location associated with the object is a location of the anatomical landmark(s) and the location of the anatomical landmark(s) is known relative to the location of the object. The location of the target is then inferred from the location of the anatomical landmark in the corresponding reference image.

The location associated with the object may be a location of the object; and the similarity may be determined based on raw image data. The image series may include one image or more images. In addition, the method may further include, during the treatment sequence, adding a treatment image to the series of reference images. In one embodiment, the method includes comparing motion of the tracked object against the series of reference images and, based thereon, smoothing the tracked motion and/or detecting a tracking error.

In various embodiments, each reference image includes multiple regions, and the method further includes, prior to the treatment sequence, processing the reference images to determine, for each region, a location associated with the object. Each treatment image may include one or more regions, and the region(s) is compared against a corresponding region in the reference images to determine similarity therebetween. The locations of the object in the treatment images are then determined based at least in part on the locations associated with the object in the corresponding regions in the corresponding reference images.

In another aspect, the invention is directed to a system for tracking one or more moving objects (including a treatment target and/or a non-treatment target) during a treatment sequence. In various embodiments, the system includes an imaging apparatus (e.g., an MRI apparatus), operable in conjunction with a treatment apparatus (e.g., an ultrasound transducer), adapted to (i) acquire a series of reference images of a region (e.g., an anatomical region) having the object (e.g., the anatomical object of interest) during motion thereof (each reference image corresponding to a different stage of the motion) prior to the treatment sequence, and (ii) acquire treatment images of the anatomical region during the treatment sequence. In addition, the system includes means for acquiring complementary information during acquisition of the treatment images and/or reference images and a computation unit configured to (i) receive complementary information, (ii) process the reference images to determine, for each reference image, a location associated with the object, (iii) correlate one or more of the treatment images to corresponding reference image(s) based on similarity therebetween and the received complementary information, and (iii) track the object in the treatment image(s) based at least in part on the location associated with the object in the corresponding reference image(s). In one embodiment, the computation unit is further configured to acquire the complementary information during acquisition of the reference images.

The means for acquiring complementary information may include an input device for receiving image metadata, a motion sensor, and/or a computational module for extracting information associated with preceding treatment (or reference) images or extrapolating information of a stage of the motion associated with a current treatment image. In addition, the computation unit may be further configured to determine an acquisition sequence of k-space data associated with the treatment images based on types of information encoded in each k-space location. For example, the computation unit may be configured to acquire the k-space data alternatively in a high-frequency region and a low-frequency region alternately.

The computation unit may be further configured to focus an ultrasound beam generated by the transducer onto the object based on the tracking. The treatment sequence may include treatment of a target other than the anatomical object; the computation unit is further configured to shape an ultrasound beam generated by the transducer so as to avoid the object based on the tracking. In some embodiments, the treatment sequence is part of a treatment procedure including multiple time-separated treatment sequences, each including one or more exposures of an anatomical target to therapeutic energy; the computation unit is further configured to use a treatment image obtained during a first one of the treatment sequences as a reference image for a subsequent second one of the treatment sequences.

In addition, the computation unit may be further configured to monitor a temperature in the anatomical region by performing baseline subtraction between the treatment images and the corresponding reference images. In various embodiments, the computation unit is further configured to identify one or more anatomical landmarks in each of the reference images; the location associated with the object is a location of the anatomical landmark(s), and the location of the anatomical landmark(s) is known relative to a location of the object. In addition, the computation unit is further configured to track the target by inferring the location of the target from the location of the anatomical landmark(s) in the corresponding reference image.

The computation unit may be configured to correlate the treatment images against the reference images based on raw image data. Additionally, the computation unit may be configured to add a treatment image to the series of reference images. Further, the computation unit is configured to compare motion of the tracked object against the series of reference images and, based thereon, smooth the tracked motion and/or detect a tracking error. In various embodiments, each reference image includes multiple regions and the computation unit is configured to process the reference images to determine, for each region, a location associated with the object prior to the treatment sequence. Each treatment image includes one or more regions, and the computation unit is further configured to compare the region(s) against a corresponding region in the reference images to determine similarity therebetween and subsequently determine the locations of the object in the treatment images based at least in part on the locations associated with the object in the corresponding regions in the corresponding reference images.

In another aspect, the invention is directed to a method for tracking a moving anatomical object during treatment. In various embodiments, the method includes, prior to the treatment, acquiring a series of reference images of an anatomical region having the anatomical object during motion thereof (each reference image corresponding to a different stage of the motion) and processing the images to determine, for each image, a location associated with the object. Further, the method includes, during the treatment: (i) performing a scanning sequence that include multiple scanning lines to acquire image data associated with the anatomical object, the scanning; (ii) acquiring complementary information associated with the anatomical object during acquisition of the image data; (iii) computing similarity between the acquired image data and the reference images to identify one or more matching reference image(s); (iv) determining whether a number of the matching reference images is below a threshold; and if so, selecting one of the matching reference image(s) based on the similarity and the complementary information, and inferring a location of the anatomical object from the location associated with the anatomical object in the selected reference image. If, however, the number of the matching reference images is above a threshold, performing the scanning sequence in a next scanning line to acquire the image data of the anatomical object based on the pre-determined scanning sequence and repeating steps (ii), (iii) and (iv).

As used herein, the term "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which:

FIGS. 5A-5D illustrate a sequence for acquiring k-space data during treatment in accordance with various embodiments;

DETAILED DESCRIPTION

The present invention provides systems and methods for tracking the motion of an object of interest, e.g., a treatment target, in real time during an image-guided procedure. The procedure may, for example, involve the application of focused ultrasound to (i.e., the sonication of) a material, a tissue or organ for the purpose of heating it, either to necrose, ablate, or otherwise destroy the tissue if it is, e.g., cancerous, or for non-destructive treatments such as pain amelioration or the controlled inducement of hyperthermia. Ultrasound may also be used for other, nonthermal types of treatment, such as, e.g., neuromodulation. Alternatively, the procedure may use different forms of therapeutic energy, such as, e.g., radio-frequency (RF) radiation, X-rays or gamma rays, or charged particles, or involve other treatment modalities such as cryoablation. Motion tracking in various treatment procedures may serve to guide the therapeutic energy beam onto the target and/or around other, non-target tissues and organs, i.e., to adjust the beam focus, profile, and/or direction based on images of the affected anatomical region, which may, in some embodiments, also visualize the beam focus. MRI is a widely used technique for such image-based motion tracking. However, other imaging techniques, including, e.g., X-ray imaging, X-ray computed tomography (CT), or ultrasound imaging, may also be used and are within the scope of the present invention. In addition, the motion tracking may be achieved using one or more two-dimensional images and/or three-dimensional images. An exemplary system for implementing methods in accordance with various embodiments is an MRgFUS system, such as the one depicted in FIG. 1, with a suitable image-processing and control facility as described in detail below with reference to FIG. 4.

Figure 2:
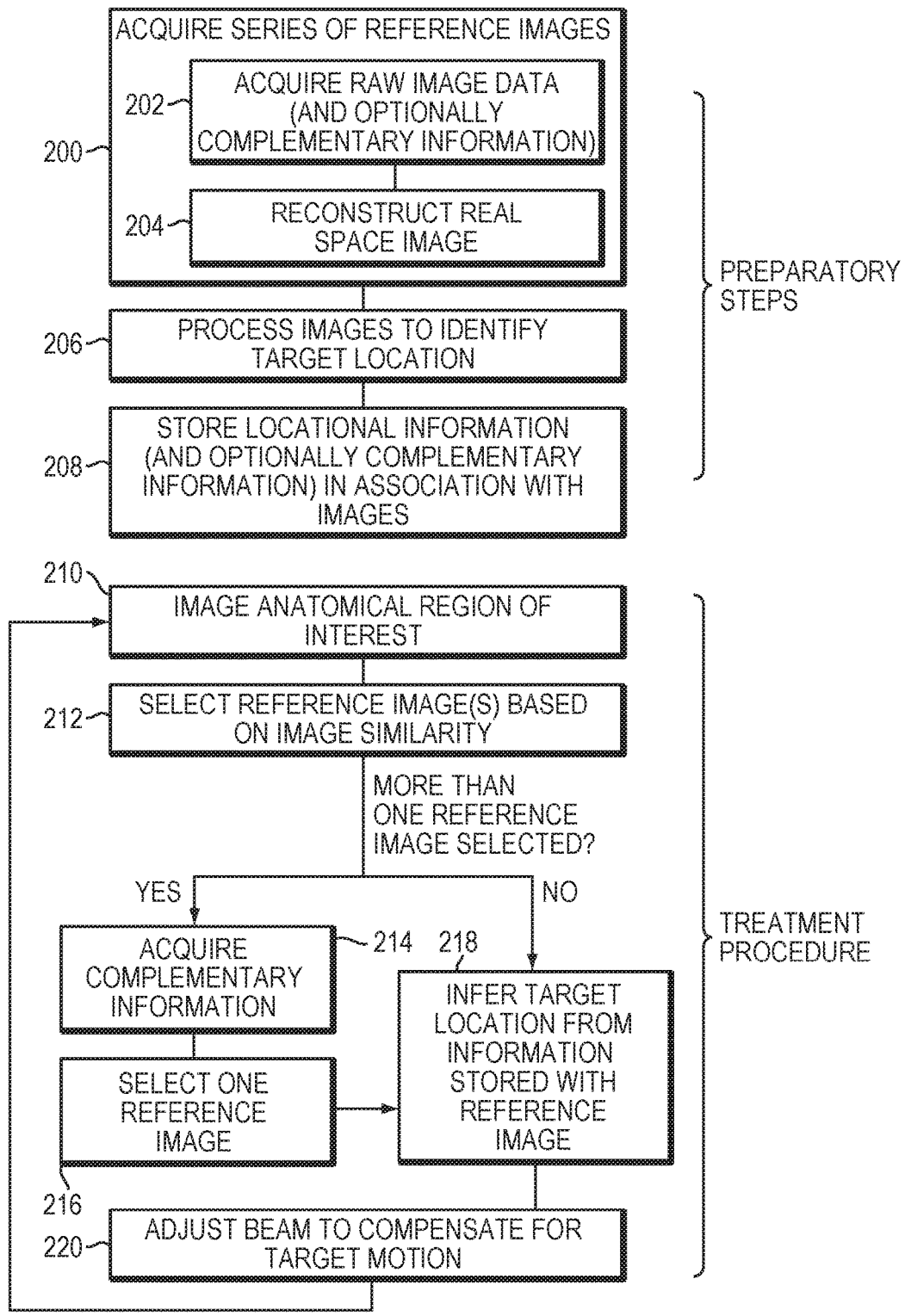
FIG. 2 is a flow chart illustrating a tracking method in accordance with various embodiments.

FIG. 2 illustrates methods for real-time motion tracking in accordance with various embodiments. For ease of reference, the following description only refers to target tracking; it should be understood, however, that the same methods generally apply as well to the tracking of other organs or tissues of interest (such as organs vulnerable to damage from the therapeutic beam) or materials. The method includes preparatory steps performed prior to the procedure of interest, as well as steps executed during the procedure. In a first preparatory step 200, a series of images of an anatomical region including the target is acquired during motion thereof. Each image typically corresponds to a different stage of motion, and the series collectively covers the anticipated range of motion. For example, the series of images may be taken at regular intervals during a complete cycle of a periodic respiratory motion or a non-periodic motion. As another example, the region of interest, e.g. the anatomical region of interest within a patient may be monitored for a certain time period to capture a range of positions resulting from inadvertent sporadic motions. In MRI-based methods, acquiring the images typically involves, first, acquiring raw k-space MR signals (step 202), and then reconstructing real-space images from the raw data (step 204). Both k-space and real-space image data are complex-valued (i.e., have a magnitude and phase or, expressed differently, real and imaginary parts). Optionally, in some embodiments, complementary information (e.g., additional image-related and/or motion-related information as further described below) may be acquired during acquisition of the raw k-space image data 202. The complementary information may be compared with the complementary information acquired during treatment to resolve ambiguity resulting from image comparison using partial data, and thereby correctly identify the reference image best matching the partial raw data and/or sub-image acquired during treatment.

In the next step 206, the real-space images are processed to determine coordinates associated with the target, such as the target coordinates themselves and/or coordinates of anatomical landmarks located at known (e.g., fixed) positions relative to the target. This step may be performed by any of a number of feature-detection or tracking methods known to those of skill in the art. In some embodiments, the target and/or landmark location is determined for each image separately in absolute coordinates within the image frame (e.g., in terms of row and column numbers) or generally in a coordinate system of the imaging system using, e.g., edge detection or blob detection. In other embodiments, relative changes in the target and/or landmark locations (expressed, e.g., in coordinate differences or translation/motion vectors) between different images are determined. For example, the location of the target in the first image of the series may arbitrarily be designated as the origin, and the location of the target in subsequent images may be measured relative to that origin. Motion vectors can be obtained by pixel-based ("direct") methods such as block-matching algorithms, phase-correlation and frequency-domain methods, pixel recursive algorithms, Bayesian estimators (e.g., a maximum a posteriori probability (MAP) estimate or a Markov random field model), and/or optical flow methods, as well as by feature-based ("indirect") methods that match corresponding features (such as, e.g., Harris corners) between images. Block-matching algorithms, for instance, involve computationally shifting a portion (or "block") of the first image by a large number of known vectors and correlating the resulting copies of the block against the subsequent image to identify the best match. Importantly, the computational cost associated with determining the target location is of reduced importance in selecting an appropriate method because the image-processing step 206 is generally carried out before, not concurrently with, target tracking in real time.

Figure 3:
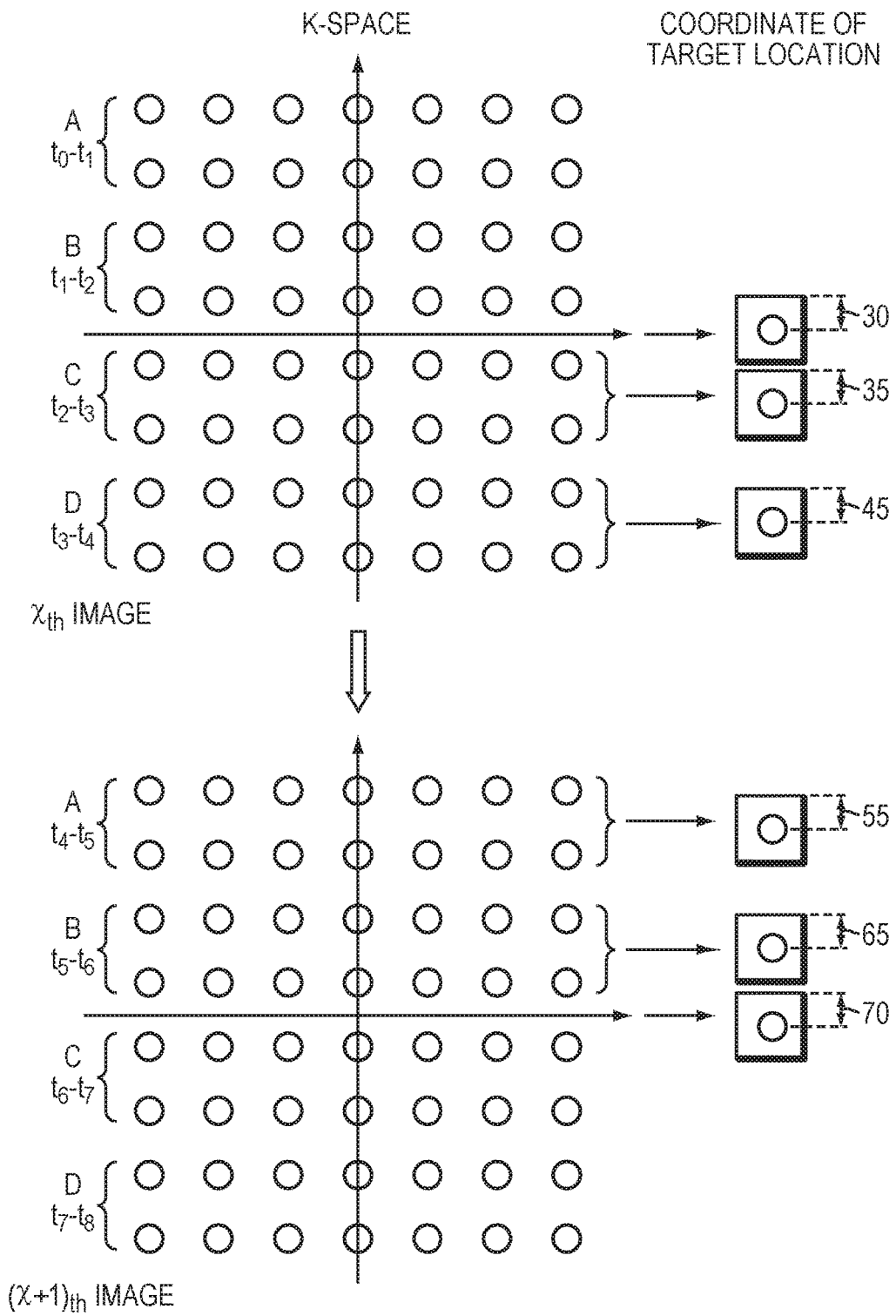
FIG. 3 depicts associating target locations with various parts of k-space image data using an interpolation approach in accordance with various embodiments.

The method may comprise MRI scanning to acquire the reference images and treatment images and the imaging apparatus may be configured to carry out Mill scanning. Typically, during MRI scanning, the k-space data is acquired in a row-by-row manner. Referring to FIG. 3, for example, in one reference image (e.g., $x^{th}$ image) of the library, the top two rows of the k-space image data may be acquired during a single shot or during the first two shots of an MRI procedure (labeled as region A) during a time period of $t_0$-$t_1$, the next two rows of data (labeled as region B) can be acquired during the next two shots during a time period of $t_1$-$t_2$, image data in a region labeled as C can be acquired by the following two shots during a period of $t_2$-$t_3$, and finally the last two shots can acquire image data in a region labeled as D during a period of $t_3$-$t_4$. Similarly, in the next reference image (e.g., $(x+1)^{th}$ image), the k-space image data is acquired in a sequential order from region A to region D. The locational information of the target derived from the two reference images represents the location of the target at the median or average time during data acquisition (i.e., $t_2$ in $x^{th}$ image and $t_6$ in the $(x+1)^{th}$ images, respectively). In instances where the target's movement is continuous and steady, it may be possible to interpolate the target's locations at an acquisition time between $t_2$ and $t_6$. For example, as depicted, if one coordinate of the target location is determined to have a value of 30 (e.g. in mm or pixels) in the $x^{th}$ reference image and 70 in the $(x+1)^{th}$ reference image, the value of the target's coordinate when acquiring image data in the regions C and D of the $x^{th}$ image may be interpolated as 35 and 45, respectively. Likewise, the value of the target's coordinate when acquiring data in regions A and B of the $(x+1)^{th}$ reference image may be interpolated as 55 and 65, respectively. The interpolation process may be performed on various regions of the reference images throughout the library such that each region of the k-space data in each reference image has its associated target location. This interpolation approach may advantageously provide a more accurate target information when partial k-space image data is acquired during treatment as further described below. Note that each region of the reference image may have the same amount or different amounts of k-space image data, and the interpolation is computed based on the length of time required for acquiring the image data in each region. In addition, the regions may overlap.

The entire k-space image data and/or real-space image data of each acquired reference image may be stored in the reference library. Alternatively, it is possible to store only a portion of the acquired k-space image data (i.e., a sub-image matrix) and/or a portion of the real-space image data (i.e., a sub-image) relating to the object of interest to reduce the storage requirement. The stored reference images may have less spatial resolution and/or a smaller image frame size than the reference images initially acquired (or reconstructed) in steps 202, 204. As used herein, the term "entire k-space data" or "k-space data initially acquired in step 200" connotes a data matrix of, for example, 16×16, 32×32, 64×64, 128×128, 128×256, 192×256, or 256×256 obtained using a standard MRI scanning procedure, and the term "partial k-space data" connotes any matrix (i.e., ordered arrangement of data) having dimensions less than the "entire k-space data."

In one embodiment, some raw data in the phase-encoding direction (i.e., rows) and/or in the frequency-encoding direction (i.e., columns) in k-space is omitted and not stored in the reference library. For example, referring to FIG. 4A, the library may include raw data located in every other row while including raw data in every single column; this may result in a 50% reduction of the frame size (sub-image) in the vertical direction of the real-space image reconstructed therefrom. In some embodiments, the sub-images are stored in the reference library as well. Although the reference library built using this approach includes sub-images, the spatial resolution of the sub-images is uncompromised—i.e., the sub-images have the same resolution as the images reconstructed from the initially acquired raw data.

In another embodiment, the raw data in the most peripheral scanning lines (or "outer region") in k-space is truncated, and only the data in a portion close to the k-space center (or "center region") is stored. For example, referring to FIG. 4B, the library may store only 50% of the raw data close to the k-space center region in the phase-encoding direction, and the remaining 50% of raw data in the outer region is discarded. Advantages of this approach include, for example, retaining the frame size of the real-space image. However, because the data at high spatial frequencies is omitted, information about edges and fine details in the real-space images may be lost; therefore, this approach may result in a resolution decrease in the reconstructed real-space images. As used herein, the "center region" may include all raw k-space data except the sequence of raw data forming the periphery in k-space. Alternatively, the "center region" may include only a fraction of the radial extent—e.g., 10%, 20%, 50%, etc. The "outer region" typically includes all raw data outside the center region.

Figure 4A:
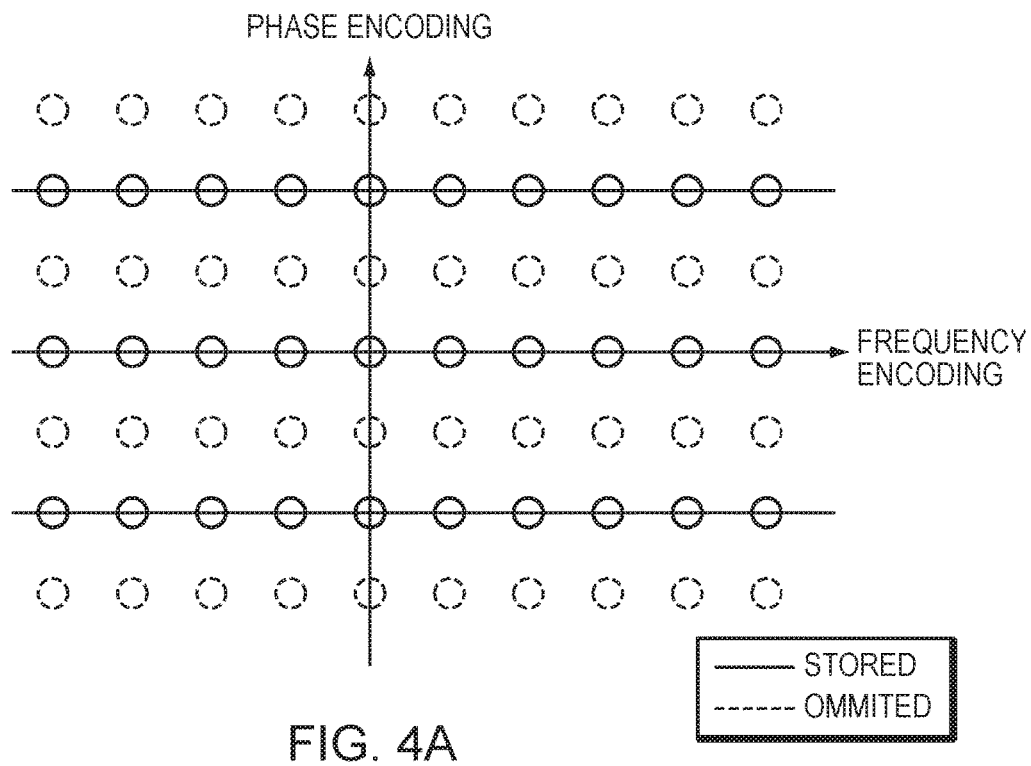
FIGS. 4A and 4B depict storing partial k-space image data in a reference library in accordance with various embodiments.
Figure 4B:
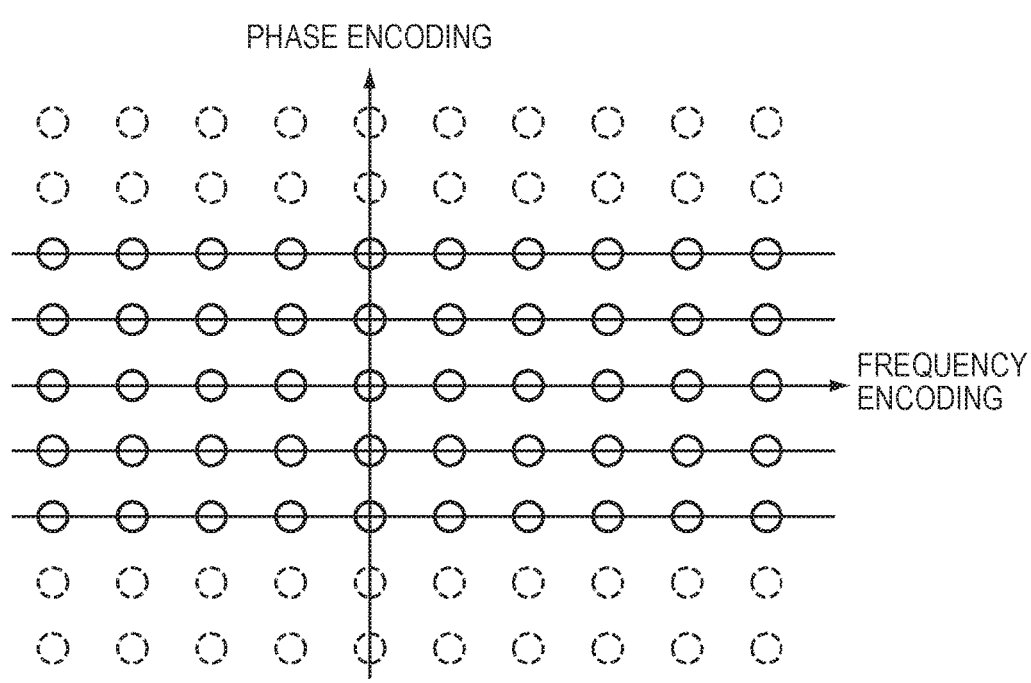

To determine whether to store the entire raw image data or only a portion thereof in the library, it is necessary to evaluate various factors, including the storage capacity, the shape and size of the object of interest, the required minimal resolution of the images, etc. For example, if the object of interest has an asymmetric shape in its length and width (e.g., a rectangular or elliptical shape) and/or the spatial resolution thereof is of an important concern, it may be suitable to store partial data in the phase-encoding direction and entire data in the frequency-encoding direction as depicted in FIG. 4A. If, however, the object of interest has comparable sizes in its length and width, and/or the detail thereof is of less importance, the reference library may store a portion of the raw data closer to the k-space center as depicted in FIG. 4B.

Referring again to FIG. 2, in a step 208, the locational information derived from the images in step 206 (including the interpolated target location associated with each region of the k-space data) and/or the complementary information acquired during acquisition of the raw k-space image data may be stored along and in association with respective (k-space and/or real-space) images in the reference library. For example, each reference image may be combined with its associated locational information into a reference record (which may include one or more data files). Alternatively, the reference images and the locational information may be stored in different data structures and/or at different memory locations, and an additional database may link each image with the associated locational information.

The reference library built in the preparatory steps 200-208 is used subsequently during the procedure of interest for real-time target tracking. This means, in some embodiments, that the preparatory steps are completed before treatment of the target commences. In other embodiments, the preparatory steps for a particular treatment sequence are taken during an earlier treatment sequence. For example, focused-ultrasound ablation of a tumor may be carried out in two or more phases: a first phase during which the central region of the tumor is targeted, and one or more subsequent phases in which the peripheral regions of the tumor are exposed to ultrasound. Since the risk to healthy tissue surrounding the tumor increases as treatment progresses, so may the need for accurate, real-time imaging. Therefore, motion tracking during the first phase may proceed at an imaging rate low enough to permit target localization by conventional means (i.e., means that do not rely on a reference library), and motion tracking during the later phase(s) may utilize the treatment images from the first phase as reference images to enable much higher imaging rates. In general, if treatment involves multiple discrete treatment sequences, the same reference library may be used for all sequences, or the reference library may be reset for each sequence using images obtained during one or more previous sequence as the new reference images. Further, in some embodiments, only a subset of the acquired reference images (e.g., every other image taken during a respiratory cycle) is processed prior to the treatment sequence of interest and used as an initial reference library for target tracking, and the remaining reference images are processed subsequently, during the treatment sequence of interest, to refine the reference library.

In various embodiments, during treatment of the target, the anatomical region of interest is imaged repeatedly (step 210), e.g., every 100 ms to create a treatment image sequence. In various embodiments, only partial raw k-space image data (or a "sub-image matrix", as opposed to the entire k-space image data acquired in step 202) is acquired during treatment for reducing the image acquisition time. The position of the (generally moving) object of interest in each image frame is determined by comparing the partial raw image data acquired during treatment against a corresponding portion of the image data stored in the reference library, and a closest matched reference image is identified using a suitable metric of image similarity (step 212). For example, referring to FIGS. 5A-5B, the k-space data in regions A, B, C, and D of the treatment image may be compared against the k-space image data in regions A, B, C, and D, respectively, of the reference images (as shown in FIG. 3) in the reference library.

Similarly, if the comparison is performed on the real-space images, the treatment sub-image may be compared with only a corresponding fraction of each of the real-space images stored in the reference images. Alternatively, an image analysis (e.g., pattern matching) may be performed to compute the similarity between the treatment sub-image or partial raw data and various portions within a reference image (since the reference image may have a larger frame size than the treatment sub-image) in order to identify a region that best matches the treatment sub-image or partial raw data within each image. Subsequently, the best-matching reference image is selected based on the similarity of the best-matching portion therein.

The image comparison may be based, for example, on k-space or real-space image data, i.e., it may involve, but does not necessarily require, the reconstruction of real-space treatment sub-images from the partial raw data acquired during treatment. Typically, the comparison is performed on a pixel-by-pixel basis, where a "pixel" refers to an element of the image data array, which generally stores amplitude and phase values as a function of real-space coordinates or k-space coordinates, respectively. Suitable similarity metrics include, for example, cross-correlation coefficients, the sum of squared intensity differences, mutual information (as the term is used in probability and information theory), ratio-image uniformity (i.e., the normalized standard deviation of the ratio of corresponding pixel values), the mean squared error, the sum of absolute differences, the sum of squared errors, the sum of absolute transformed differences (which uses a Hadamard or other frequency transform of the differences between corresponding pixels in the two images), or complex cross-correlation (for complex images, such as MRI images), and other techniques familiar, to those of skill in the art, in connection with image registration.

In some embodiments, the similarity between the treatment sub-image (or partial raw data) and the closest reference image, as measured by the chosen similarity metric, is compared against a (metric-specific) similarity threshold, and only if the level of similarity surpasses that of the threshold (which typically means, for metrics that measure the differences, i.e., the dissimilarity, between images, that the value of the metric falls below the threshold value) is the reference image considered a match for the treatment sub-image. In other embodiments, the reference image most similar to the treatment image is deemed a match regardless of the absolute degree of similarity.

Figure 5C:
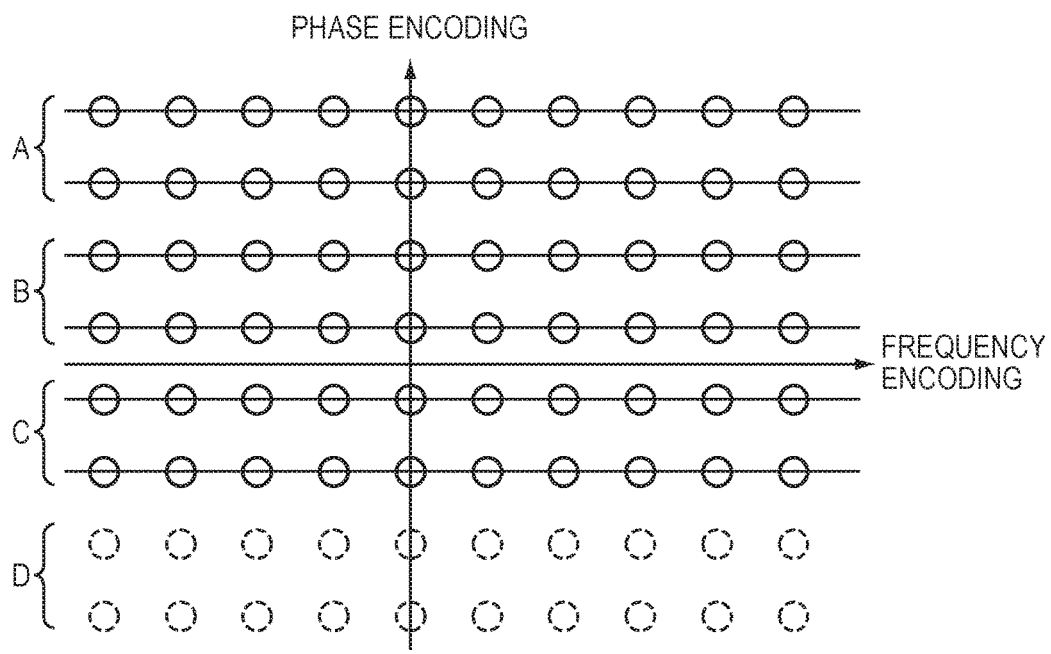
Figure 5D:
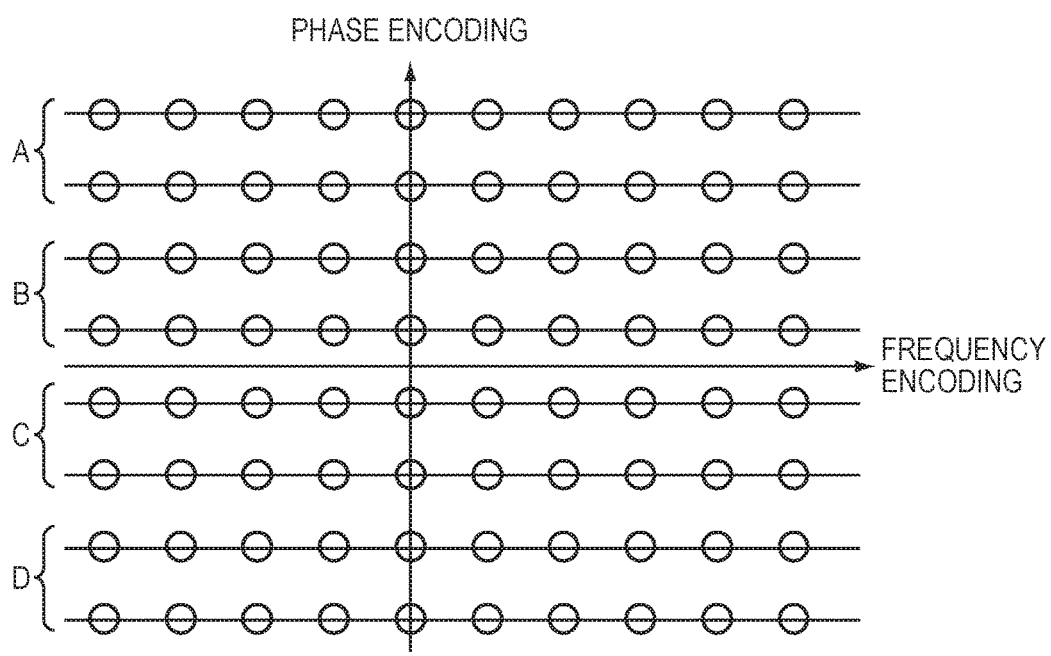

Referring again to FIGS. 5A-5D, during treatment, the k-space may be divided into multiple regions, e.g., regions A-D. Upon acquisition of image data in region A, a matching process (i.e., comparing the acquired image data against the corresponding image data—that is, the image data in region A—of the reference images stored in the library) is substantially simultaneously performed to identify one or more reference images that "match" the acquired treatment image data. If the number of identified reference image(s) is below a pre-determined threshold (e.g., less than 5 reference images are identified as matching treatment image), complementary information (e.g., additional image-related and/or motion-related information) as further described below may be provided to determine one reference image that best matches the treatment image. If, however, the number of identified reference images exceeds the pre-determined threshold, the data-acquisition process—i.e., acquiring the image data in region B—continues. The data-acquisition process may further continue (e.g., acquiring data in region C as shown in FIG. 5C followed by acquiring data in region D as shown in FIG. 5D) until the number of reference images identified to match the treatment image data falls below the pre-determined threshold. It should be stressed, of course, that the exemplary sequences for k-space data acquisition depicted in FIGS. 5A-5D are for illustrative purposes only, and that any acquisition sequence may be used in order to optimize the quality of treatment image and reduce the data-acquisition time.

In addition, the size of each region in the treatment image may include one or more rows of data and may dynamically vary. For example, if a preceding treatment image requires acquisition of image data in regions A and B in order to reduce the number of "matching" reference images to be less than the pre-determined threshold, the area of region A in the current treatment image may expand to include half the area of region B in the preceding treatment image. If, however, image data in region A of the preceding treatment image is sufficient to identify a number of reference image(s) that is less than the pre-determined threshold, the area of region A in the current image may be reduced to half the size of that in region A of the preceding treatment image. Further, image data acquisition and processing may be performed sequentially or simultaneously. For example, while the image data in region A is processed to identify reference image(s) in the library, image data in region B may be acquired simultaneously.

Figure 6:
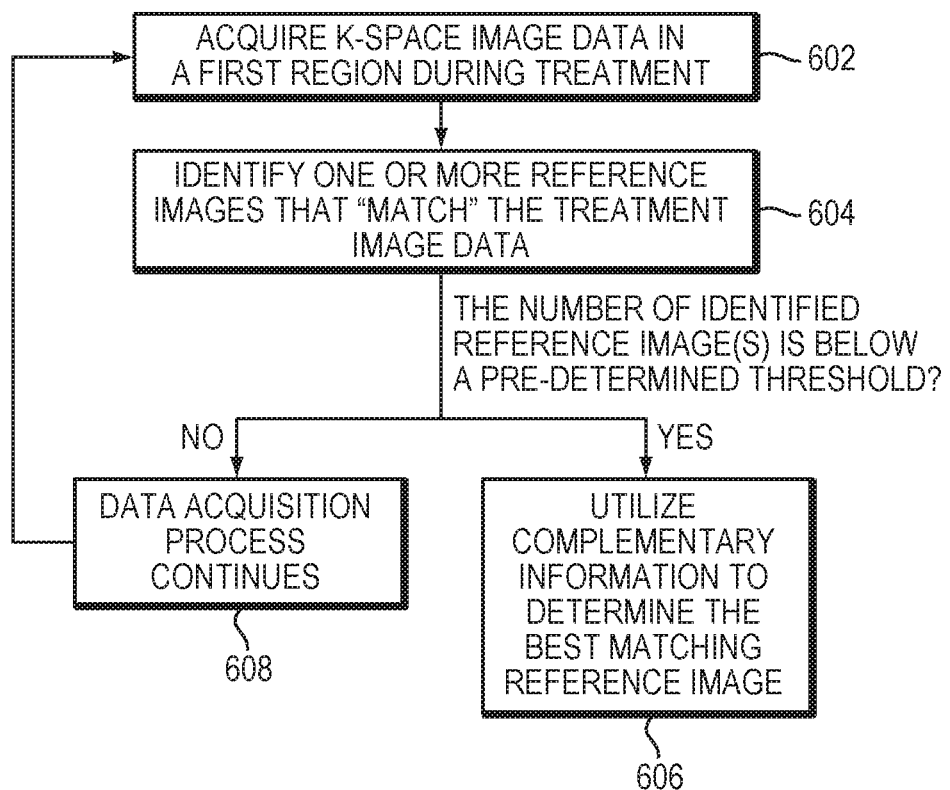
FIG. 6 is a flow chart depicting a method of identifying a reference image that matches image data acquired during treatment in accordance with various embodiments.

FIG. 6 is a flow chart 600 illustrating acquisition and process of image data in a treatment image in accordance with various embodiments. In a first step 602, k-space image data in a first region is acquired during treatment. In a second step 604, the acquired image data (in k-space or real-space) is substantially simultaneously processed to identify one or more matching reference images. If the number of identified reference image(s) is below a pre-determined threshold, complementary information is provided to determine one reference image that best matches the treatment image (in a step 606). If, however, the number of identified reference images exceeds the pre-determined threshold, the data-acquisition process continues—i.e., acquiring image data in the next region (in a step 608). Steps 602, 604, 608 can be iteratively implemented until the number of reference images identified in step 604 falls below the pre-determined threshold. Again, the amount and locations of raw k-space data in each region acquired during treatment may vary dynamically.

Because acquisition of k-space image data is a relatively long process compared with computing the similarity between two image matrices, this approach advantageously allows the image acquisition time (for tracking) during treatment to be reduced by acquiring only partial k-space image data while identifying the reference image that best matches the acquired treatment data, thereby providing the location of the object(s) of interest in the current treatment image from the matching reference image as further described below.

Figure 7A:
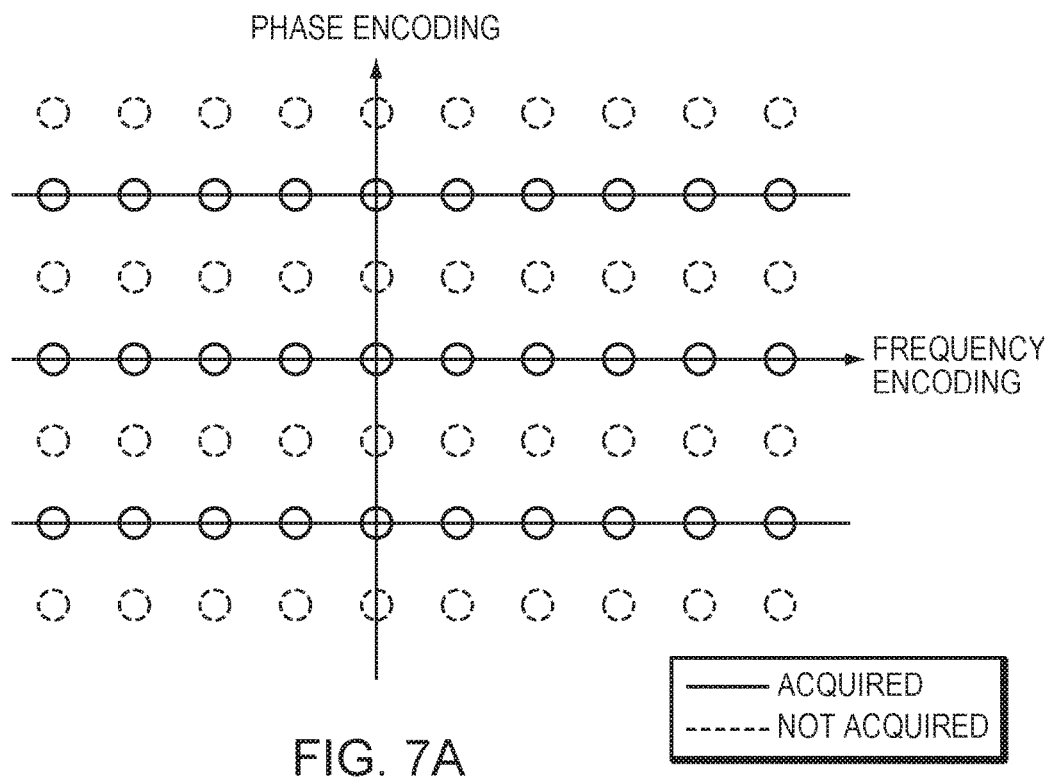
FIGS. 7A-7C depict acquiring partial k-space image data during treatment in accordance with various embodiments.

Generally, as described above, the reference library stores the entire raw data initially acquired in step 200, but only partial k-space data is required for tracking during treatment. In some embodiments, the reference library stores partial raw data, and during treatment, the raw k-space data is acquired based on the partial data stored in the reference library. Regardless of the amount of image data stored in the reference library, various approaches may be implemented to acquire partial k-space data during treatment. For example, referring to FIG. 7A, the k-space image data used for tracking may be acquired with fewer scanning lines in the phase-encoding direction (e.g., acquired every other row) while data in the frequency-encoding direction is acquired in every column to reduce the image-acquisition time. The frame size of the real-space image reconstructed from the reduced amount of raw data decreases 50% in the vertical direction, but the spatial resolution of the real-space image is the same as that of images having image data from every row. Therefore, this approach is suitable for imaging an anatomical region having an asymmetric shape (i.e., having a length differing significantly from the width). Note, however, that it is possible to acquire partial raw data using this approach even when the anatomical region has a comparable length and width. In instances where the anatomical region has a width larger than the vertical field of view of the image, a foldover artifact may appear. In various embodiments, this artifact is eliminated (or at least reduced) using any suitable technique (such as applying MRI sequence that selectively saturates the areas surrounding the region of interest).

Figure 7B:
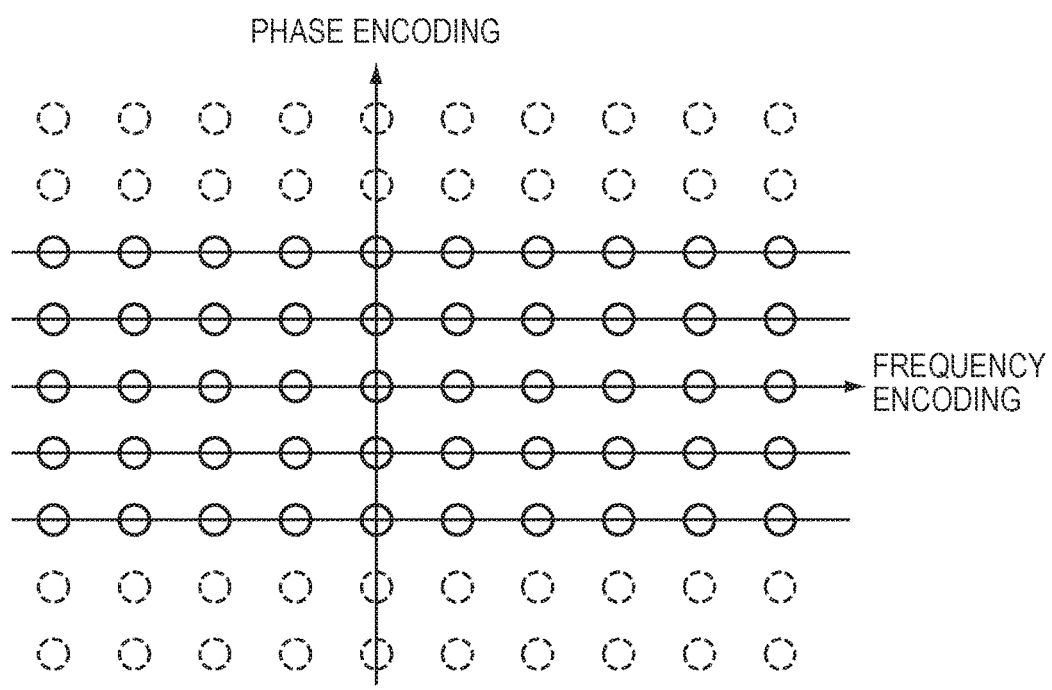

In another embodiment, a percentage of the imaging scanning is reduced—i.e., only a portion of k-space is scanned to reduce the image-acquisition time during treatment. For example, referring to FIG. 7B, only data points located in the center region of k-space in the phase-encoding direction are acquired while the remaining data located in the outer region in the phase-encoding direction is not acquired. Although this approach may result in lower resolution in the real-space images due to omission of the data at high spatial frequencies, the frame size of the real-space image advantageously remains unchanged (corresponding to that of images including both high- and low-frequency data).

Figure 7C:
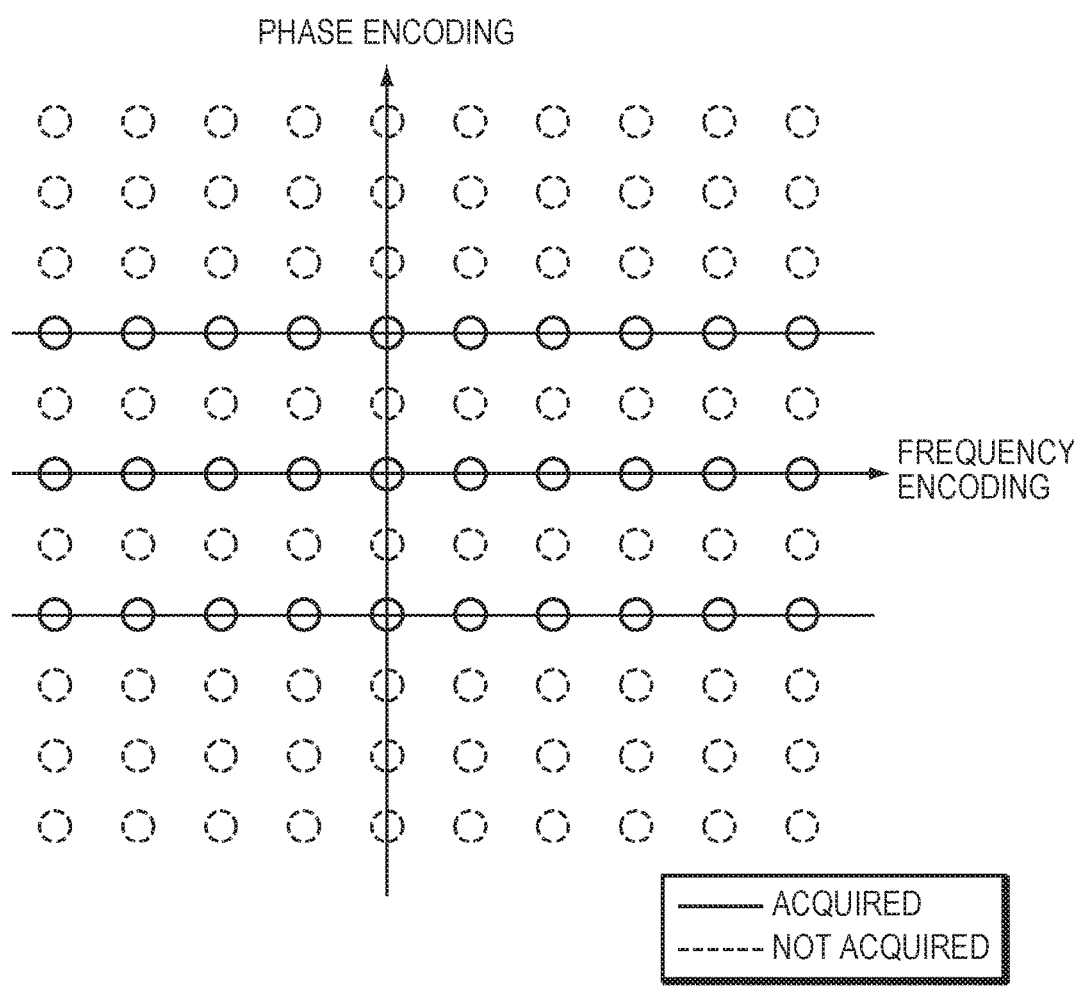

Referring to FIG. 7C, in still another embodiment, the k-space image data is acquired using a combination of the approaches described in FIGS. 7A and 7B—i.e., only data located in the center region of k-space is acquired and the data in the center region is acquired with fewer scanning lines in the phase-encoding direction while data in the frequency-encoding direction is acquired in every column.

Because every data point in the k-space matrix contains a portion of the information necessary to reconstruct a complete real-space image, reducing the k-space data may result in less spatial resolution and/or a smaller frame size of the real-space images. For example, acquiring less k-space data at high spatial frequencies may cause the reconstructed image to have less information regarding the borders and contours as well as structure detail, whereas acquiring less k-space data at low spatial frequencies may result in less image contrast. If the treatment images have less resolution and/or smaller frame size, the result may be ambiguity when attempting to identify the best-matching reference image—i.e., more than one reference image may be identified.

Figure 8:
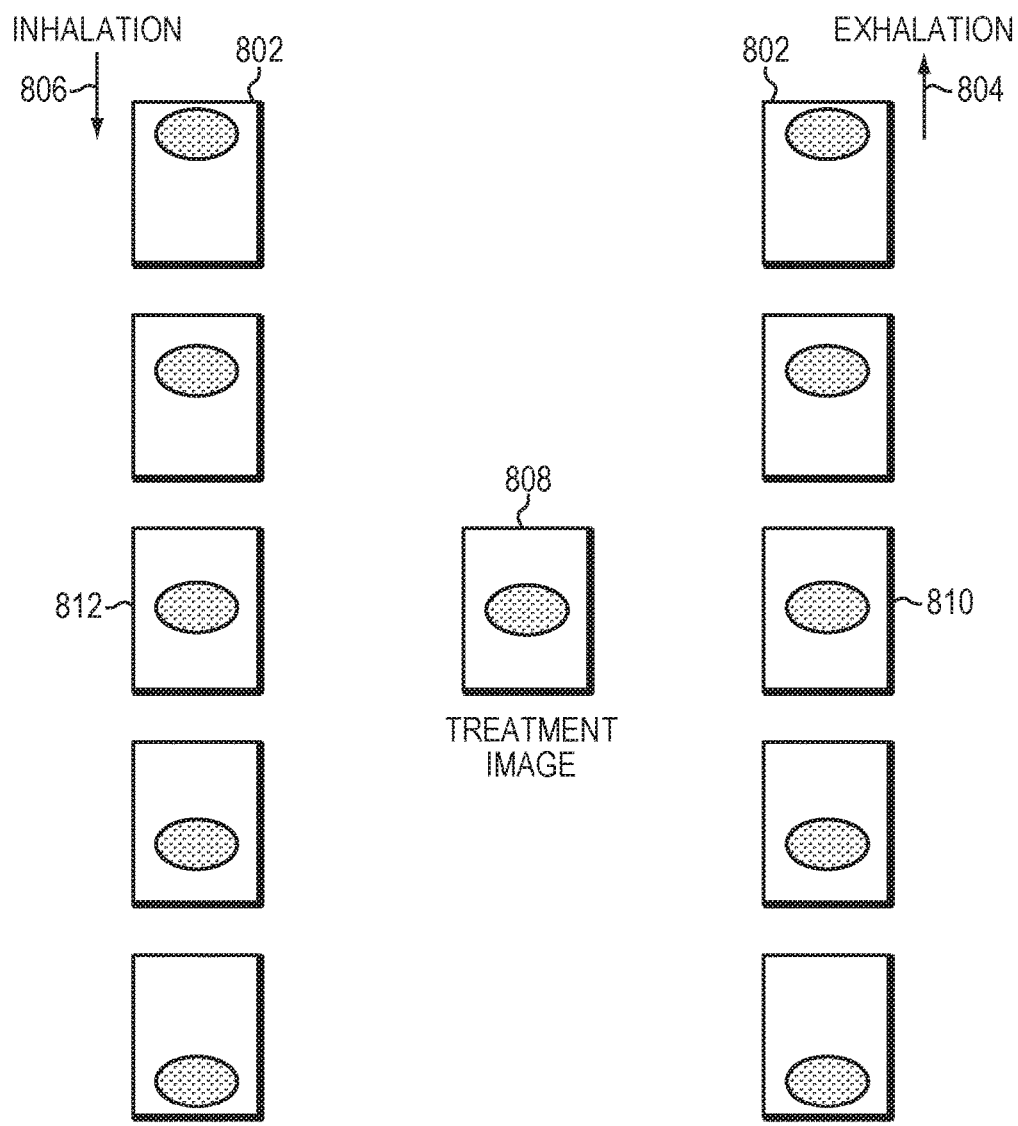
FIG. 8 depicts a treatment image and the reference images in a library in accordance with various embodiments.

For example, referring to FIG. 8, the reference library may include a series of reference images 802 of an anatomical region of interest obtained at time-separated intervals during a respiratory cycle, including an exhalation stage 804 and an inhalation stage 806. If a sub-image or an image with less resolution 808 is acquired during treatment, there may be two reference images—e.g., one image 810 obtained during the exhalation stage 804 and another image 812 obtained during the inhalation stage 806—found to have high and relatively equivalent similarity to the treatment image.

Figure 1:
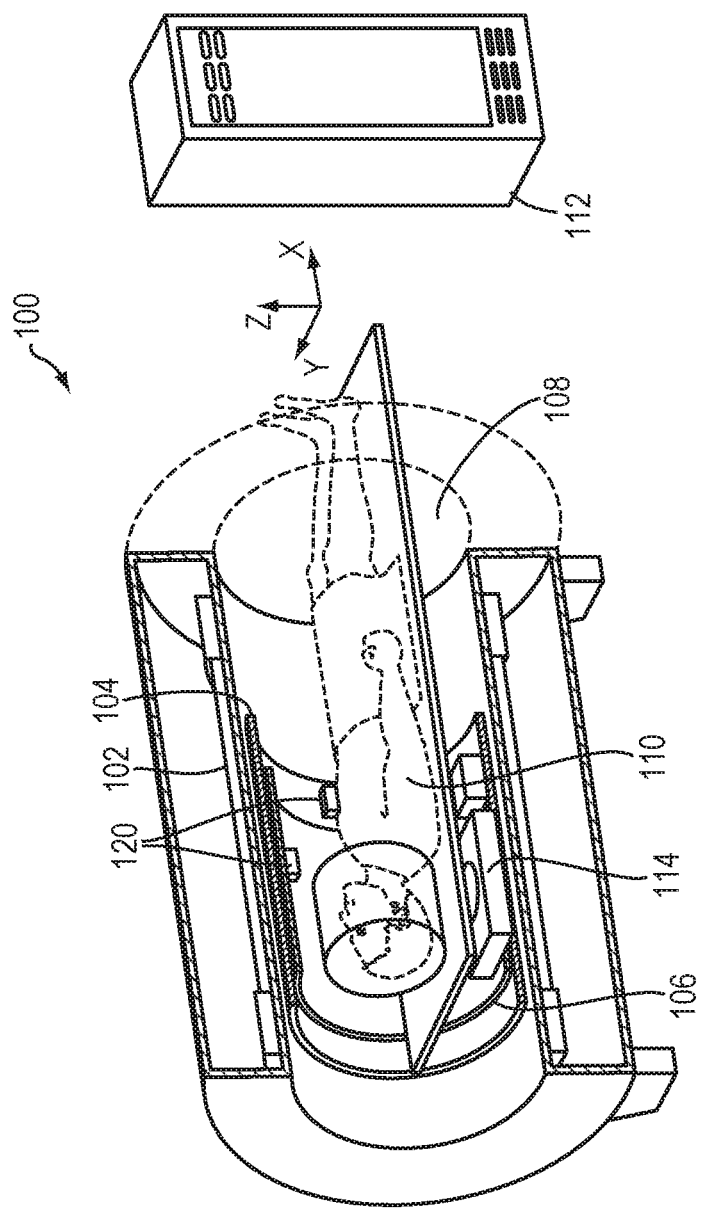
FIG. 1 illustrates an MRI-guided focused ultrasound system in accordance with various embodiments.

Referring again to FIG. 2, in various embodiments, the object of interest is tracked by other means substantially simultaneously during acquisition of the treatment image in order to provide complementary information (such as image-related and/or motion-related information), which can resolve ambiguity among the reference images (step 214). In one embodiment, a complementary tracking system 120 is implemented in the MRI apparatus 100 or is attached to the patient (as shown in FIG. 1) to provide the complementary information. For example, a motion sensor (e.g, a respiration monitor belt) may be strapped around the patient's chest to provide information about the stage of respiration cycle; this information is then used to select the best-matching reference image among the multiple reference images identified in previous steps 210, 212 (step 216). For example, if the respiration monitor belt indicates that the patient is in the inhaling stage, the image 812 in FIG. 8 is determined to be the reference image that best matches the treatment image. This may be achieved, for example, by including metadata with the images indicating when during the respiratory cycle it was obtained. In other embodiments, the complementary information acquired during treatment is compared against the complementary information stored in the reference library. Based on the comparison of the complementary information and the image similarity, the reference image that best matches the partial raw data (and/or sub-image) and the complementary information acquired during treatment is identified.

Alternatively, the complementary information may be provided by the target's movement identified in the preceding images. For example, if analysis of the preceding few treatment images indicates that the target is inhaling, the matching reference image is selected from the images corresponding to (e.g., marked with metadata specifying) the inhalation stage only. Thus, in the situation of FIG. 8, the ambiguity is resolved and reference image 812 is determined to be the best-matching reference image.

In instances where there is still more than one reference image identified to be matching the current treatment image even after taking the complementary information into account, the treatment procedure may, in some embodiments, continue for a brief period (e.g., for one or two image frames), and if matching reference images are identified for subsequently acquired treatment images, delays in the procedure are avoided. During that time, the ultrasound beam may stay stationary or be directed (e.g., by predictive algorithm) based on recent resolved tracking points. However, if it is unsafe to skip an image, or if too many successive procedure images cannot be matched against any of the reference-library images, the procedure is either aborted or interrupted until the target location has been ascertained (e.g., by conventional, computationally more expensive means) and resumed thereafter.

Figure 9A:
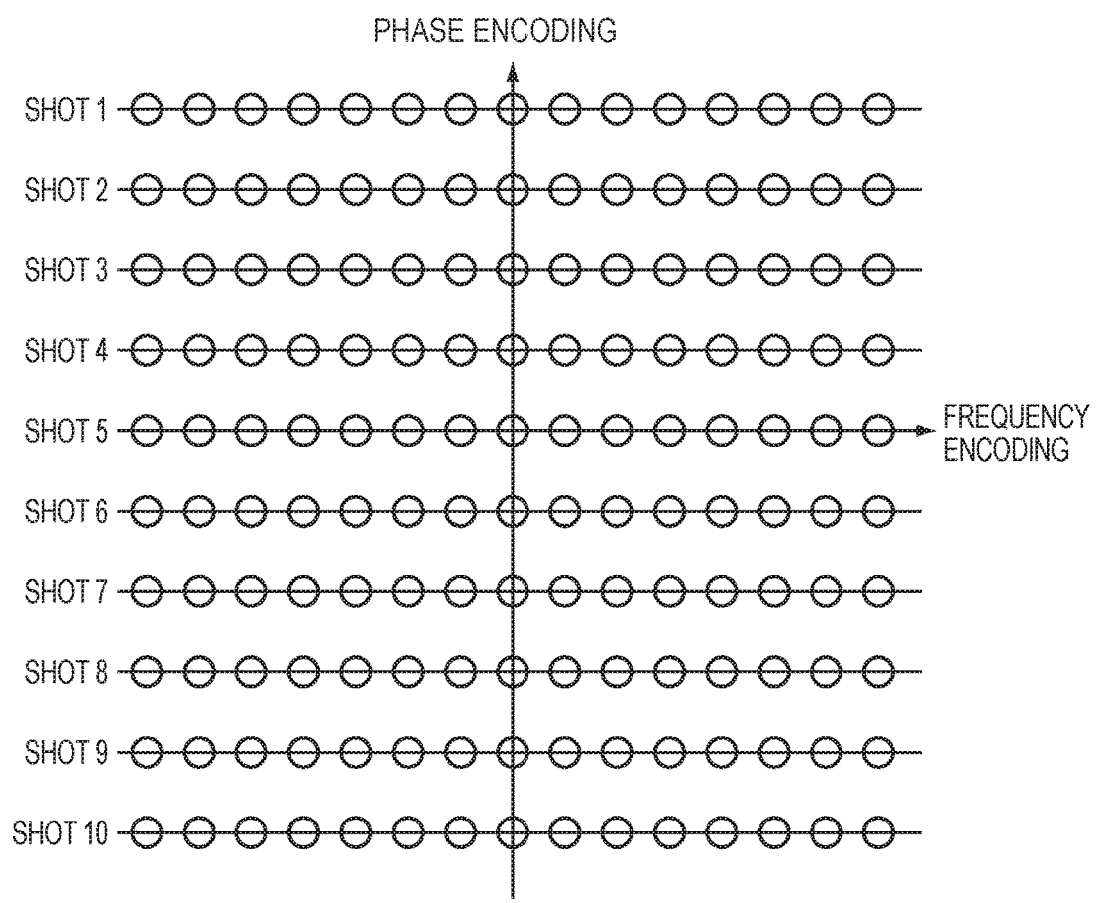
FIG. 9A depicts a conventional method of acquiring k-space image data.
Figure 9B:
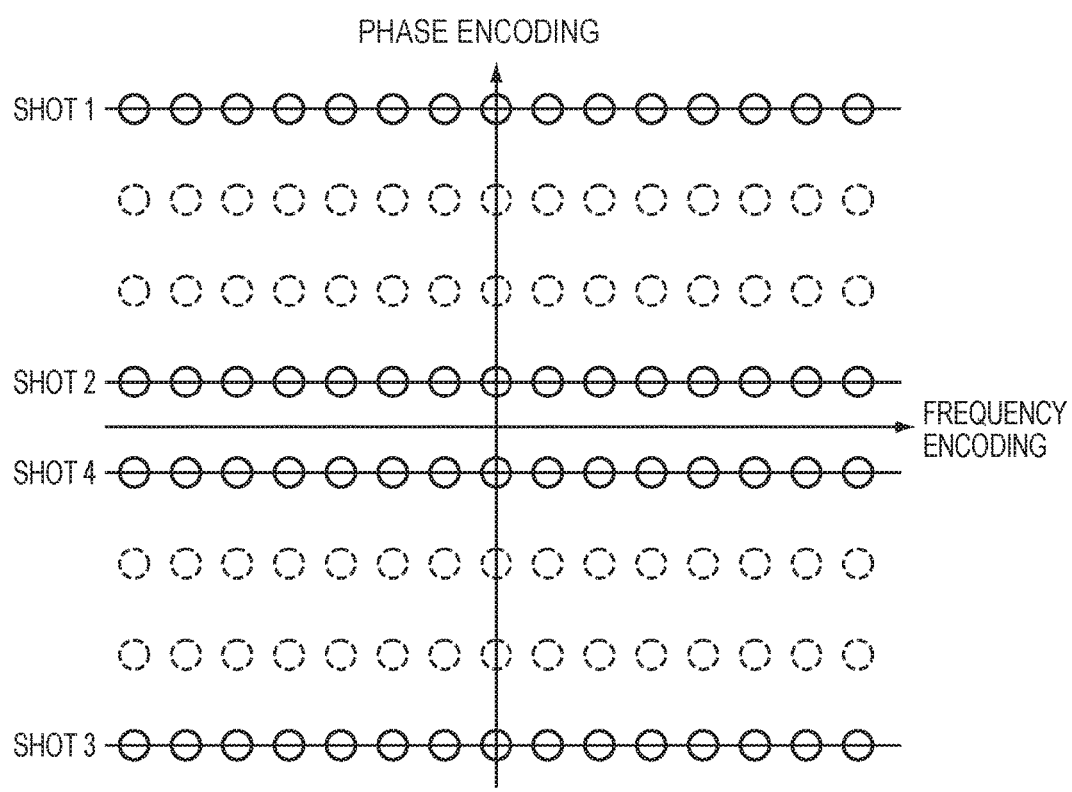
FIGS. 9B and 9C illustrate various sequences for acquiring k-space data during treatment in accordance with various embodiments.
Figure 9C:
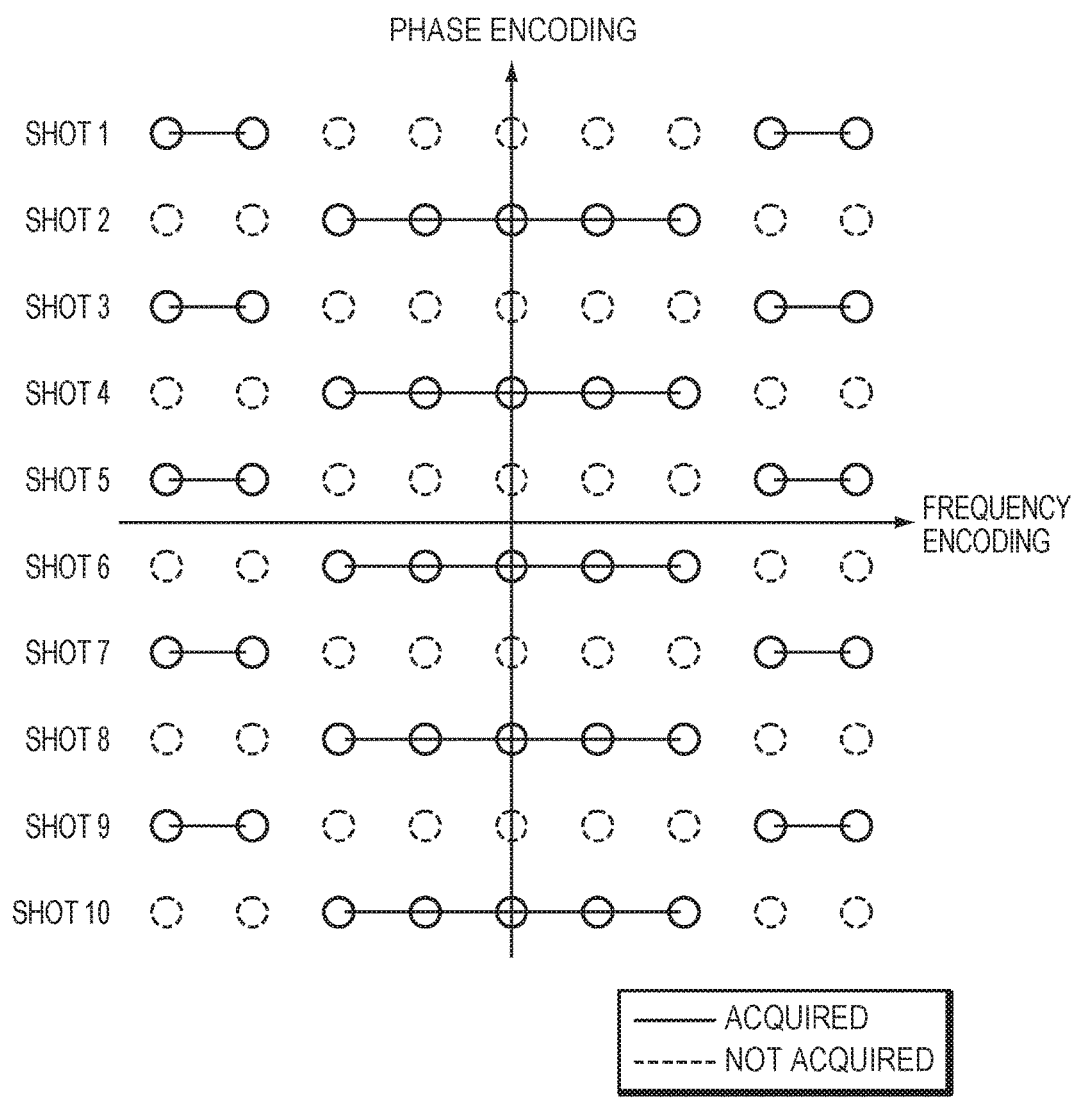

With reference to FIG. 9A, typically during MRI scanning, the k-space data is acquired in a continuous, row-by-row manner; this acquisition sequence, however, may not be efficient to track a moving anatomical object of interest in real time. In various embodiments, the sequence of data acquisition in k-space during treatment is determined based on the types of information encoded in each k-space location. For example, referring to FIG. 9B, in one embodiment, the k-space image data is acquired alternately in the large phase-encoding region and small phase-encoding region. In another embodiment, referring to FIG. 9C, the k-space image data is acquired alternately in the high-frequency region and low-frequency region in a row-by-row (or any other suitable) manner.

Figure 9D:
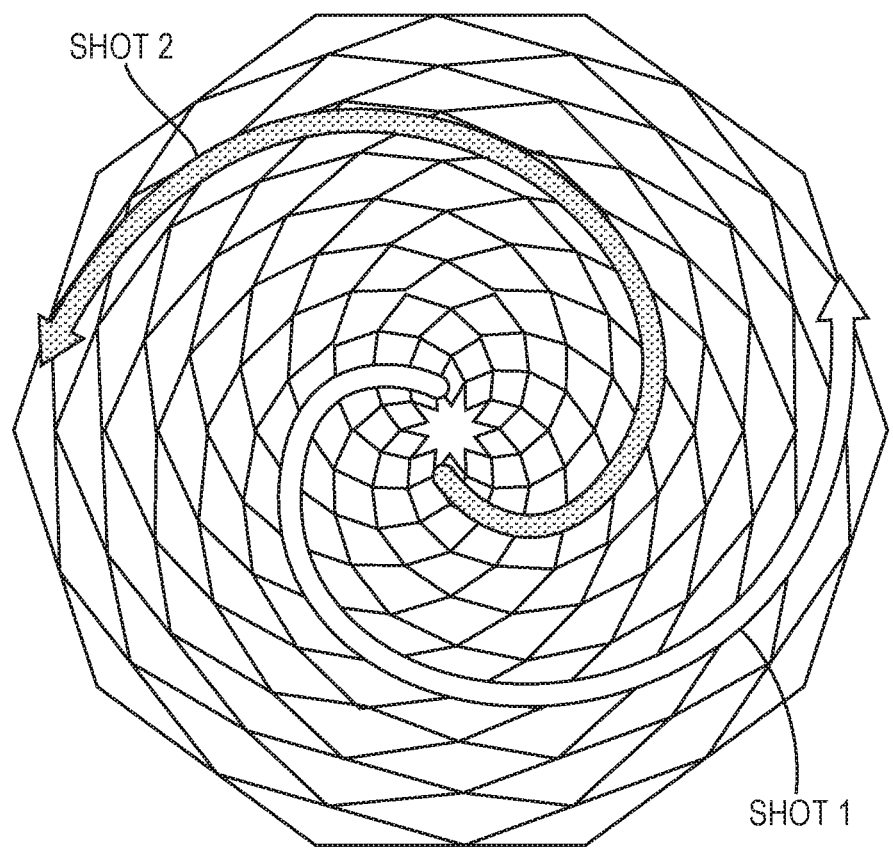
FIG. 9D depicts another conventional method of acquiring k-space image data.

In various embodiments, and with reference to FIG. 9D, the k-space data is acquired in a spiral manner. Acquisition of partial k-space data during treatment as described above may apply to this scanning approach as well. For example, image data acquired from the first shot may be compared against the corresponding image data (i.e., image data located on the same spiral trajectory) stored in the reference library to identify one or more matching reference images. In addition, the number and locations of the scanning shots may vary in order to reduce delay of data acquisition while allowing the location of the treatment target or other objects of interest to be tracked in real time.

Referring again to FIG. 2, once a matching reference image has been identified, the location of the target can be readily inferred from the previously determined locational information associated with that reference image (step 218). For example, if the stored locational information includes or consists of the target coordinates themselves, these coordinates are taken to be the coordinates of the target in the current treatment image. Thus, the target can be tracked in real time without the need to identify the target or other landmark in reconstructed treatment images. Further, in some embodiments, treatment-image reconstruction itself is unnecessary if each treatment image is correlated to one of the reference images based on the raw data of both images, or a portion thereof. For example, referring again to FIGS. 3 and 5A, if the k-space data in region A of the $(x+1)^{th}$ image (as shown in FIG. 3) is identified to best match the image data in region A of the treatment image (as shown in FIG. 5), the coordinates of the target location in the treatment image are inferred from the coordinates of the target location associated with region A in the $(x+1)^{th}$ reference image. Therefore, one coordinate of the target location in the treatment image of FIG. 5A has a value of 55 that is associated with region A of the $(x+1)^{th}$ reference image. The interpolation approach may thus advantageously allows the target location to be more accurately identified during treatment, especially when only partial k-space data is acquired and used for comparison against the partial raw data in the reference library.

Based on the tracked target coordinates, the ultrasound (or other therapeutic energy) beam may be steered during the treatment procedure to compensate for any target motion (step 220). Similarly, if non-target organs or tissues are tracked, their coordinates may be used to steer and/or shape the ultrasound (or other energy) beam so as to avoid or minimize their exposure of to the therapeutic energy. Particularly, organs vulnerable to damage from the acoustic beam are often of high interest, and the positions of such organs can be taken into account during beam-forming such that the energy beam is shaped so as to heat the target while avoiding damage to sensitive adjacent organs as they move.

In some embodiments, the reference library is extended based on images obtained in real time during a procedure. For example, if a newly acquired image reveals the position of the target (or other object of interest) to be outside the region collectively represented in the initial reference library, the newly acquired image may be analyzed to determine the location of the target, and added to the reference library along with the locational information. Optionally, treatment may be paused during the image processing and resumed once the image analysis is complete. In extreme cases, the reference library may even be empty at the beginning of a procedure, and reference images may be added successively as the procedure is carried out. This facilitates a design trade-off between accuracy at the expense of computational overhead (where the library is large, for example, and contains images from previous sessions) or computational efficiency when the reduction in accuracy is clinically acceptable (e.g., where reference images from previous sessions are unlikely to be relevant to a current treatment sequence, in which case the reference library is built up during the current sequence).

In applications where the tracked target motion is periodic (such as during a respiratory cycle), reference images are typically taken sequentially during the cycle of motion, and tracking accuracy during the treatment procedure can, thus, be improved by filtering the tracking results against the reference library. For example, the curve that describes target motion over time during treatment may be compared against and smoothed based on the target motion over time during acquisition of the reference library. Furthermore, target motion as reflected in images of the reference library can serve to detect faulty tracking results, e.g., when, at certain points in time, the tracked target seems to move against the trend of motion during that period in the cycle.

In some embodiments, imaging during a procedure is simultaneously used to quantitatively monitor in vivo temperatures. This is particularly useful in MR-guided thermal therapy (e.g., MRgFUS treatment), where the temperature of a treatment area (e.g., a tumor to be destroyed by heat) should be continuously monitored in order to assess the progress of treatment and correct for local differences in heat conduction and energy absorption to avoid damage to tissues surrounding the treatment area. The monitoring (e.g., measurement and/or mapping) of temperature with MR imaging is generally referred to as MR thermometry or MR thermal imaging.

Among various methods available for MR thermometry, the proton resonance frequency (PRF) shift method is often the method of choice due to its excellent linearity with respect to temperature change, near-independence from tissue type, and temperature map acquisition with high spatial and temporal resolution. The PRF shift method is based on the phenomenon that the MR resonance frequency of protons in water molecules changes linearly with temperature (with a constant of proportionality that, advantageously, is relatively constant between tissue types). Since the frequency change with temperature is small, only −0.01 ppm/° C. for bulk water and approximately −0.0096 to −0.013 ppm/° C. in tissue, the PRF shift is typically detected with a phase-sensitive imaging method in which the imaging is performed twice: first to acquire a baseline PRF phase image prior to a temperature change and then to acquire a second phase image after the temperature change—i.e., a treatment image—thereby capturing a small phase change that is proportional to the change in temperature. A map of temperature changes may then be computed from the (reconstructed, i.e., real-space) images by determining, on a pixel-by-pixel basis, phase differences between the baseline image and the treatment image, and converting the phase differences into temperature differences based on the PRF temperature dependence while taking into account imaging parameters such as the strength of the static magnetic field and echo time (TE) (e.g., of a gradient-recalled echo).

If the temperature distribution in the imaged area at the time of acquisition of the baseline image is known, the temperature-difference map can be added to that baseline temperature in order to obtain the absolute temperature distribution corresponding to the treatment image. In some embodiments, the baseline temperature is simply uniform body temperature throughout the imaging region. More complicated baseline temperature distributions are, in some embodiments, determined prior to treatment by direct temperature-measurements in various locations in combination with interpolation and/or extrapolation based on a mathematical fit (e.g., a smooth, polynomial fit).

Figure 10A:
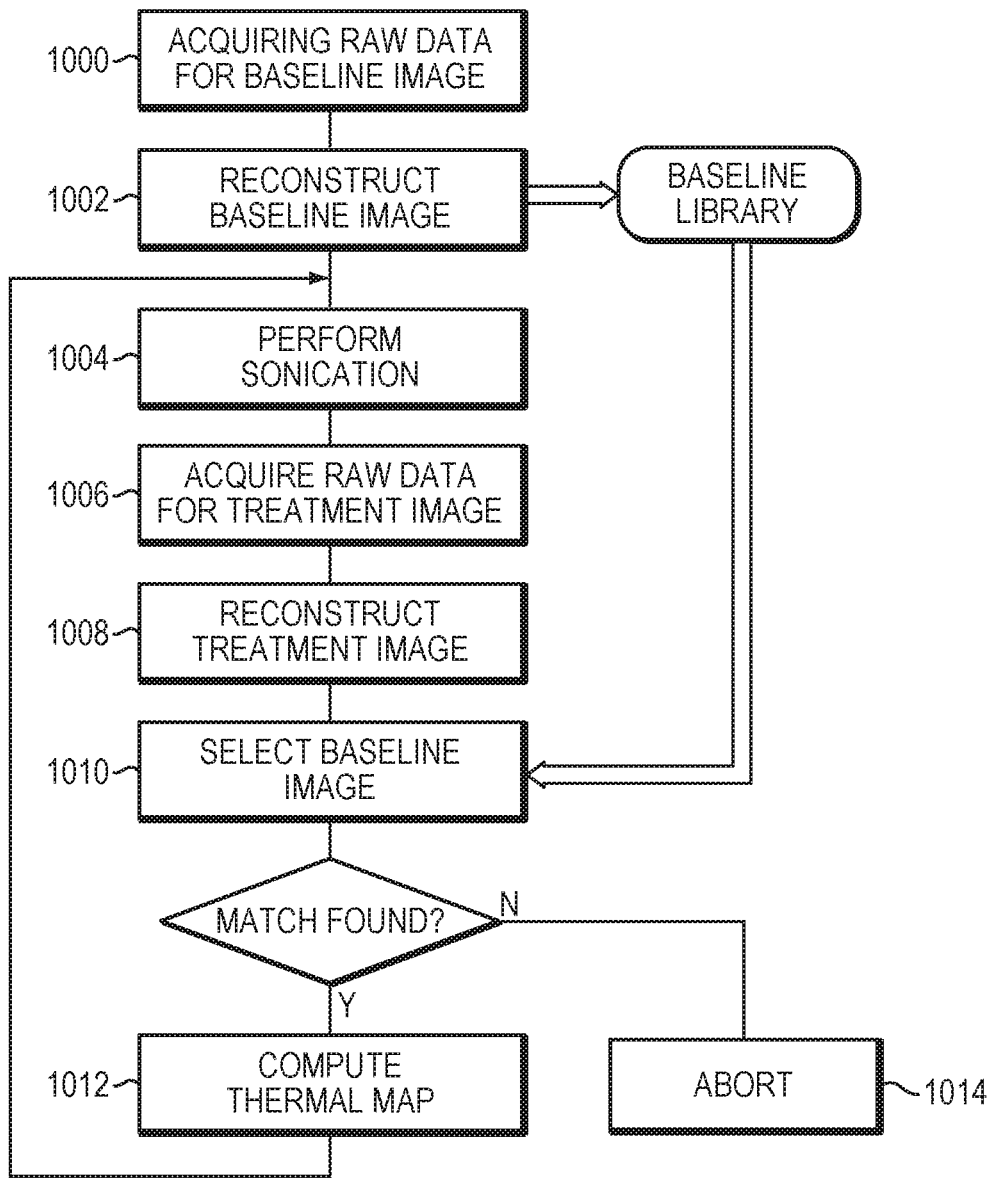
FIG. 10A is a flow chart illustrating a conventional thermometry method.

In the context of MR thermometry, motion tracking can be accomplished by obtaining a library of reference images, as described above, that covers the anticipated range of a periodic or a non-periodic motion and provides baseline phase maps corresponding to the temperature in the anatomical region prior to treatment. To determine the temperature map for a treatment image, a spatially aligned baseline image is identified (using any of the methods listed above), and the selected baseline and treatment images are then processed to determine the change in temperature. This method is often referred to as multi-baseline thermometry. In its conventional implementation, which is illustrated in FIG. 10A, multibaseline thermometry involves acquiring a library of (real-space) baseline images prior to the sonication or other temperature-affecting treatment (steps 1000, 1002), performing the sonication (step 1004), acquiring raw image data for the treatment region and reconstructing real-space images therefrom (steps 1006, 1008), selecting a suitable reference image from the baseline library (step 1010), e.g., based on an image-similarity criterion and/or complementary information provided by other tracking means, and computing the thermal map from the treatment and reference images (step 1012). If no baseline image sufficiently matches the treatment image, e.g., because the target has moved outside the region covered by the images, the process is aborted (step 1014) or alternatively, the process of library extension is initiated as described above. Otherwise, the temperature can continue to be monitored by repeated image acquisition, reference selection, and processing.

Figure 10B:
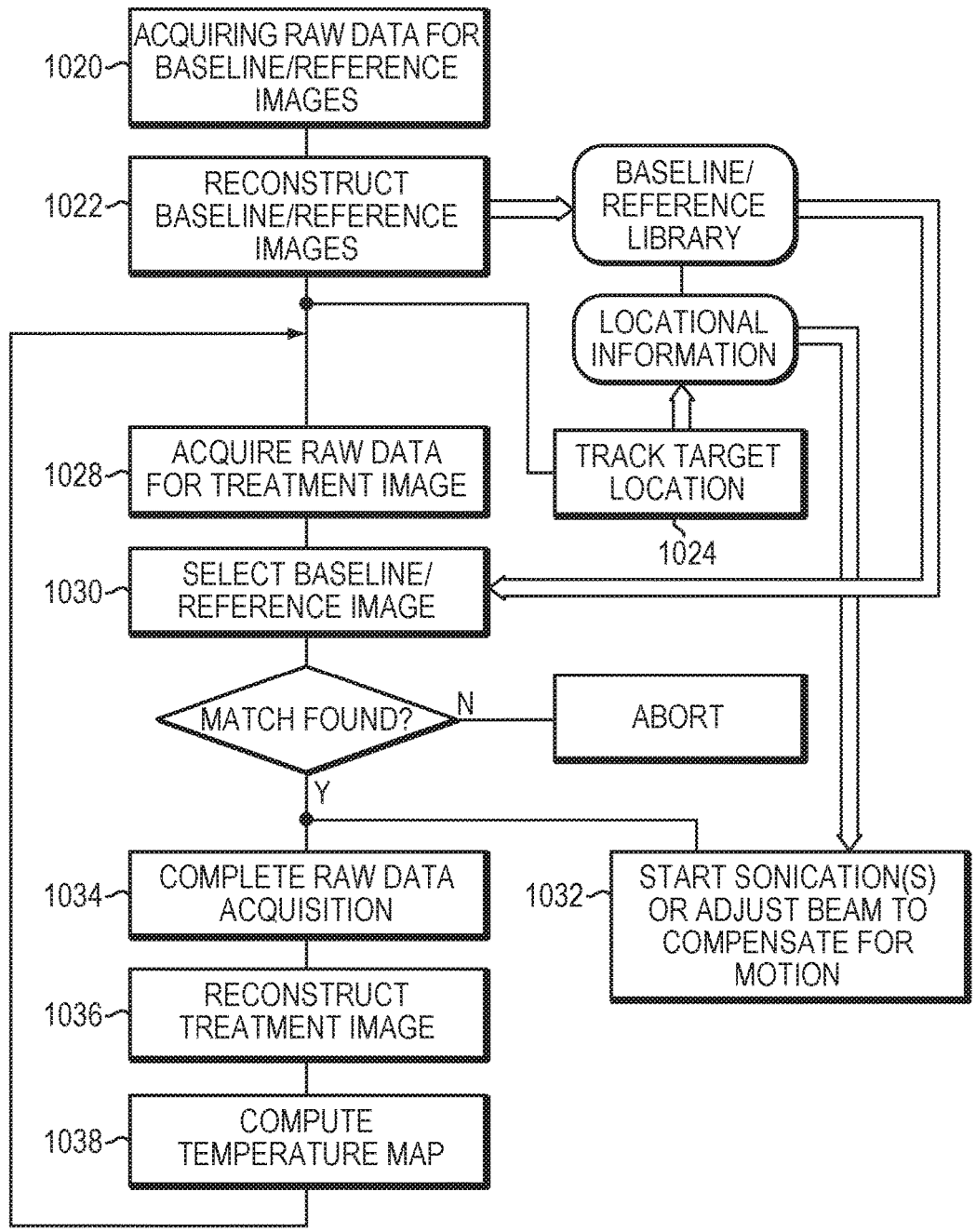
FIG. 10B is a flow chart illustrating a method for thermometry in conjunction with target tracking in accordance with various embodiments.

FIG. 10B illustrates a method that combines motion tracking for the purpose of beam adjustment and thermometry in accordance with an embodiment of the present invention. Again, a library of reference/baseline images that covers the anticipated range of a periodic or a non-periodic motion is created prior to treatment by acquiring raw image data during different stages of motion (step 1020) and optionally reconstructing the real-space reference/baseline images therefrom (step 1022). The target (and/or other anatomical object or feature of interest) is tracked in these images (step 1024), e.g., relative to a readily identifiable anatomical landmark, by way of image correlation against computationally shifted copies of prior images, complementary information provided by other tracking means, or by any of the methods described above. The identified target location (e.g., row and column numbers within the image or coordinates in some other coordinate system) is stored along or in association with each respective reference image (e.g., in a joint data record, or in a separate database whose entries are linked to the reference images). During the treatment, image data is acquired for the treatment region (step 1028), and a reference/baseline image is selected based on similarity (step 1030). As shown, the image data used for comparison with the baseline library need not constitute reconstructed real-space images. Rather, and more typically, raw (k-space) data (of both the treatment image and the baseline images) may be used to identify a suitable reference image. In some embodiments, it is not necessary to collect a complete k-space image; instead, partial raw data is used for the purpose of reference selection.

Based on the selected reference image and the target coordinates associated therewith, the sonication or other treatment procedure may start or be adjusted (step 1032), e.g., by beam shaping and/or beam steering, to ensure that the beam focus remains on the target. Further, to facilitate thermometry, the acquisition of raw image data for the treatment region may be completed (step 1034) (if has not been done already), and the real-space image may be reconstructed (step 1036) and further processed in a manner known to those of skill in the art to yield a temperature map (step 1038). In addition, the data acquired in step 1034 can be used to provide additional information for more-updated tracking. The imaging and temperature-mapping process may then be repeated for the same or another sub-sonication (i.e., one of a sequence of sonications within the overall sonication procedure). As illustrated, it is possible to reshape or redirect the therapeutic energy beam (step 1032) prior to reconstruction of the real-space image (step 1036). This way, treatment (e.g., sonication), imaging, and image processing can be performed in parallel, reducing the overall treatment time.

Figure 11:
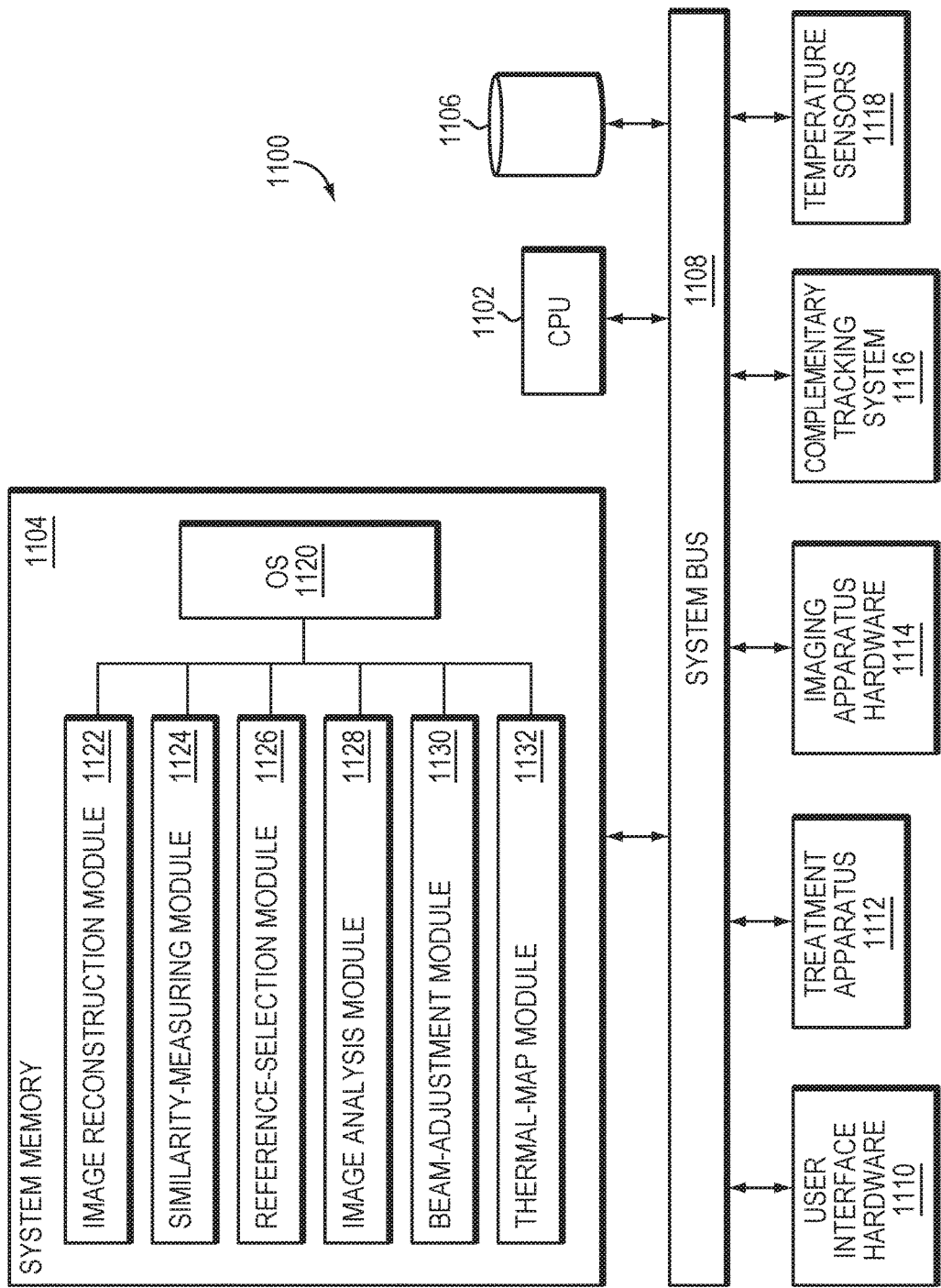
FIG. 11 is a block diagram illustrating an image-processing and control facility in accordance with various embodiments.

Motion-tracking methods in accordance herewith can be implemented using an (otherwise conventional) image-guided treatment system, such as the MRgFUS system 100 depicted in FIG. 1, in conjunction with a complementary tracking system 120 and a suitable image-processing and control facility (e.g., integrated with computation unit 112) in communication with the treatment apparatus (e.g., the beam former setting the phases and amplitudes of an ultrasound transducer array) and the imaging apparatus. The image-processing and control facility may be implemented in any suitable combination of hardware, software, firmware, or hardwiring. FIG. 11 illustrates an exemplary embodiment where the facility is provided by a suitably programmed general-purpose computer 1100. The computer includes a central processing unit (CPU) 1102, system memory 1104, and non-volatile mass storage devices 1106 (such as, e.g., one or more hard disks and/or optical storage units). The computer 1100 further includes a bidirectional system bus 1108 over which the CPU 1102, memory 1104, and storage devices 1106 communicate with each other and with internal or external input/output devices, such as traditional user interface components 1110 (including, e.g., a screen, a keyboard, and a mouse) as well as the treatment apparatus 1112, the imaging apparatus 1114, the complementary tracking system 1116, and (optionally) any temperature sensors 1118 facilitating absolute-temperature measurements.

The system memory 1104 contains instructions, conceptually illustrated as a group of modules, that control the operation of CPU 1102 and its interaction with the other hardware components. An operating system 1120 directs the execution of low-level, basic system functions such as memory allocation, file management and operation of mass storage devices 1106. At a higher level, one or more service applications provide the computational functionality required for image-processing, motion tracking, and (optionally) thermometry. For example, as illustrated, the system may include an image-reconstruction module 1122 for reconstructing real-space images from raw image data received from the imaging apparatus 1114, a similarity-measuring module 1124 for measuring similarity between treatment and reference images (whether raw or reconstructed images), and a reference-selection module 1126 for selecting suitable reference images based on the measured similarity and optionally the complementary information received from the complementary tracking system 1116 and/or locational and/or stage information provided by an image analysis module 1128. The image analysis module 1126 extracts locational and/or stage information of the target and/or other object(s) of interest from the reconstructed reference images. In addition, the system may include a beam-adjustment module 1130 for computing phase shifts or other parameters of the treatment apparatus to compensate for any detected motion, and a thermal-map module 1132 that subtracts reference from treatment images to obtain a temperature difference map and, if the absolute temperature corresponding to the selected reference baseline is known, an absolute-temperature map for the treatment image. The various modules may be programmed in any suitable programming language, including, without limitation, high-level languages such as C, C++, C#, Ada, Basic, Cobra, Fortran, Java, Lisp, Perl, Python, Ruby, or Object Pascal, or low-level assembly languages; in some embodiments, different modules are programmed in different languages.

Although the present invention has been described with reference to establishing the reference library prior to treatment, acquiring a new image sequence during treatment, and tracking a moving anatomical object by performing imaging matching between the treatment image and the reference images stored in the library, it is not intended that the motion tracking of the anatomical object should be performed during treatment only. Rather, the above-described approaches may be implemented in any application for tracking a moving target when two stages of procedures are involved—the reference library may be built in one stage where an image rate is of less or no concern and the new image sequence is acquired in another stage where a real-time image rate is preferred.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method for tracking at least one moving anatomical object during a treatment sequence, the method comprising:
    (a) prior to the treatment sequence, (i) acquiring a series of reference images of an anatomical region comprising the anatomical object during motion thereof, each reference image corresponding to a different stage of the motion, and (ii) processing the images to determine, for each image, a location associated with the object; and
    (b) during the treatment sequence, (i) acquiring treatment images of the anatomical region, the treatment images containing less information than the reference images, (ii) acquiring complementary information indicative of the stage of the motion during acquisition of the treatment images, (iii) correlating at least one of the treatment images to a corresponding reference image based on similarity therebetween and the complementary information, and (iv) tracking the object in the at least one treatment image based at least in part on the location associated with the object in the corresponding reference image; wherein the reference images and treatment images are MRI images.

2. The method of claim 1, wherein the complementary information comprises at least one of a stage of the motion, motion-sensor data, or information associated with preceding images.

3. The method of claim 2, wherein the information associated with preceding treatment images is metadata specifying when during a respiratory cycle the images were obtained.

4. The method of claim 1, wherein the images are MRI images, and a sequence for acquiring k-space data associated with the treatment images is determined based on types of information encoded in each k-space location.

5. The method of claim 4, wherein the k-space data associated with the treatment images is acquired in a high-frequency region and a low-frequency region alternately.

6. The method of claim 1, wherein the treatment sequence comprises treatment of the anatomical object.

7. The method of claim 1, wherein the treatment sequence comprises steering a focused ultrasound beam onto the object based on the tracking.

8. The method of claim 1, wherein the treatment sequence comprises treatment of a target other than the anatomical object.

9. The method of claim 8, further comprising, during the treatment, shaping a focused ultrasound beam onto the target so as to avoid the anatomical object based on the tracking.

10. The method of claim 1, wherein the at least one anatomical object comprises a treatment target and a non-treatment target.

11. The method of claim 1, wherein the treatment sequence is part of a treatment procedure comprising a plurality of time-separated treatment sequences each comprising at least one exposure of an anatomical target to therapeutic energy, wherein at least one of the acquired reference images used during a treatment sequence is a treatment image obtained during a previous treatment sequence.

12. The method of claim 11, wherein each exposure is subjection of the anatomical target to acoustic energy.

13. The method of claim 1, further comprising monitoring a temperature in the anatomical region by performing baseline subtraction between the treatment images and the corresponding reference images.

14. The method of claim 1, wherein processing the reference images comprises identifying at least one anatomical landmark in each of the reference images, the location associated with the object being a location of the at least one anatomical landmark, the location of the at least one anatomical landmark being known relative to a location of the object.

15. The method of claim 14, wherein tracking the target comprises inferring the location of the target from the location of the anatomical landmark in the corresponding reference image.

16. The method of claim 1 wherein the location associated with the object is a location of the object.

17. The method of claim 16, wherein similarity is determined based on raw image data.

18. The method of claim 1, wherein the series comprises at least one image.

19. The method of claim 18, wherein the series comprises a plurality of images.

20. The method of claim 1, further comprising, during the treatment sequence, adding a treatment image to the series of reference images.

21. The method of claim 1, further comprising comparing motion of the tracked object against the series of reference images and, based thereon, smoothing the tracked motion.

22. The method of claim 1, further comprising comparing motion of the tracked object against the series of reference images and, based thereon, detecting a tracking error.

23. The method of claim 1, wherein each reference image comprises a plurality of regions, the method further comprising, prior to the treatment sequence, processing the reference images to determine, for each region, a location associated with the object.

24. The method of claim 23, wherein each treatment image comprises at least one region, and the at least one region is compared against a corresponding region in the reference images to determine similarity therebetween.

25. The method of claim 24, wherein the locations of the object in the treatment images are determined based at least in part on the locations associated with the object in the corresponding regions in the corresponding reference images.

26. The method of claim 1, further comprising acquiring the complementary information during acquisition of the reference images.

27. A system for tracking at least one moving anatomical object during a treatment sequence, the system comprising:

(a) an imaging apparatus, operable in conjunction with a treatment apparatus, for (i) acquiring, prior to the treatment sequence, a series of reference images of an anatomical region comprising the object during motion thereof, each reference image corresponding to a different stage of the motion, and (ii) acquiring treatment images of the anatomical region during the treatment sequence, the treatment images containing less information than the reference images;

(b) means for acquiring complementary information indicative of the stage of the motion during acquisition of the treatment images; and (b) a computation unit configured to (i) receive complementary information, (ii) process the reference images to determine, for each reference image, a location associated with the object, (iii) correlate at least one of the treatment image to a corresponding reference image based on similarity therebetween and the received complementary information, and (iii) track the object in the at least one treatment image based at least in part on the location associated with the object in the corresponding reference image; wherein the reference images and treatment images are MRI images.

28. The system of claim 27, wherein the means for acquiring complementary information comprises at least one of an input device for receiving image metadata, a motion sensor, or a computational module for extracting information associated with preceding treatment images or extrapolating information of a stage of the motion associated with a current treatment image.

29. The system of claim 27, wherein the imaging apparatus comprises an MRI apparatus, and the computation unit is further configured to determine an acquisition sequence of k-space data associated with the treatment images based on types of information encoded in each k-space location.

30. The system of claim 29, wherein the computation unit is configured to acquire the k-space data alternatively in a high-frequency region and a low-frequency region alternately.

31. The system of claim 27, wherein the treatment apparatus comprises an ultrasound transducer.

32. The system of claim 31, wherein the computation unit is further configured to focus an ultrasound beam generated by the transducer onto the object based on the tracking.

33. The system of claim 31, wherein the treatment sequence comprises treatment of a target other than the anatomical object, the computation unit further being configured to shape an ultrasound beam generated by the transducer so as to avoid the object based on the tracking.

34. The system of claim 27, wherein the treatment sequence is part of a treatment procedure comprising a plurality of time-separated treatment sequences each comprising at least one exposure of an anatomical target to therapeutic energy, the computation unit being configured to use a treatment image obtained during a first one of the treatment sequences as a reference image for a subsequent second one of the treatment sequences.

35. The system of claim 27, wherein the computation unit is further configured to monitor a temperature in the anatomical region by performing baseline subtraction between the treatment images and the corresponding reference images.

36. The system of claim 27, wherein the computation unit is further configured to identify at least one anatomical landmark in each of the reference images, the location associated with the object being a location of the at least one anatomical landmark, the location of the at least one anatomical landmark being known relative to a location of the object.

37. The system of claim 36, wherein the computation unit is further configured to track the target by inferring the location of the target from the location of the anatomical landmark in the corresponding reference image.

38. The system of claim 27, wherein the computation unit is configured to correlate the treatment images against the reference images based on raw image data.

39. The system of claim 27, wherein the computation unit is further configured to add a treatment image to the series of reference images.

40. The system of claim 27, wherein the computation unit is further configured to compare motion of the tracked object against the series of reference images and, based thereon, smooth the tracked motion.

41. The system of claim 27, wherein the computation unit is further configured to compare motion of the tracked object against the series of reference images and, based thereon, detect a tracking error.

42. The system of claim 27, wherein each reference image comprises a plurality of regions, the computation unit is further configured to, prior to the treatment sequence, process the reference images to determine, for each region, a location associated with the object.

43. The system of claim 42, wherein each treatment image comprises at least one region, and the computation unit is further configured to compare the at least one region against a corresponding region in the reference images to determine similarity therebetween.

44. The system of claim 43, wherein the computation unit is further configured to determine the locations of the object in the treatment images based at least in part on the locations associated with the object in the corresponding regions in the corresponding reference images.

45. The system of claim 27, wherein the computation unit is further configured to acquire the complementary information during acquisition of the reference images.

46. A method for tracking a moving anatomical object during treatment, the method comprising:

(a) prior to the treatment,
  (i) acquiring a series of reference images of an anatomical region comprising the anatomical object during motion thereof, each reference image corresponding to a different stage of the motion; and
  (ii) processing the images to determine, for each image, a location associated with the object; and (b) during the treatment,
  (i) performing a scanning sequence to acquire image data associated with the anatomical object, the scanning sequence comprising a plurality of scanning lines; wherein the reference images are MRI images, and treatment image data is MRI data;
  (ii) acquiring complementary information associated with the anatomical object during acquisition of the treatment image data;
  (iii) computing similarity between the acquired treatment image data and the reference images to identify at least one matching reference image; wherein the treatment image data contains less information than the reference images;
  (iv) determining whether a number of the matching reference images is below a threshold; and
  if so, selecting one of the matching reference images based on the similarity and the complementary information, and inferring a location of the anatomical object from the location associated with the anatomical object in the selected reference image;

if not, based on the pre-determined scanning sequence, performing the scanning sequence in a next scanning line to acquire the image data of the anatomical object and repeating steps (ii), (iii) and (iv).

* * * * *